(12) United States Patent
Oshiyama et al.

(10) Patent No.: US 9,099,659 B2
(45) Date of Patent: Aug. 4, 2015

(54) ORGANIC ELECTROLUMINESCENT ELEMENT MATERIAL, ORGANIC ELECTROLUMINESCENT ELEMENT, DISPLAY DEVICE, AND LIGHTING DEVICE

(71) Applicant: Konica Minolta, Inc., Tokyo (JP)

(72) Inventors: Tomohiro Oshiyama, Hachioji (JP); Eisaku Katoh, Hachioji (JP); Noriko Yasukawa, Hachioji (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 13/965,909

(22) Filed: Aug. 13, 2013

(65) Prior Publication Data
US 2013/0338362 A1    Dec. 19, 2013

Related U.S. Application Data

(63) Continuation of application No. 11/994,046, filed as application No. PCT/JP2006/311260 on Jun. 6, 2006, now abandoned.

(30) Foreign Application Priority Data

Jul. 1, 2005   (JP) .................... 2005-193697

(51) Int. Cl.
H01L 51/54      (2006.01)
C07F 15/00      (2006.01)
C09K 11/06      (2006.01)
C07D 207/00     (2006.01)
C07D 403/04     (2006.01)
H01L 51/00      (2006.01)
C07D 231/12     (2006.01)
C07D 233/58     (2006.01)
C07D 401/14     (2006.01)
C07D 405/04     (2006.01)
C07D 405/14     (2006.01)
C07D 409/04     (2006.01)
C07D 409/14     (2006.01)
C07D 413/04     (2006.01)
C07D 413/14     (2006.01)
C07D 417/04     (2006.01)
C07D 417/14     (2006.01)
H05B 33/14      (2006.01)
H01L 51/50      (2006.01)

(52) U.S. Cl.
CPC .......... H01L 51/0085 (2013.01); C07D 231/12 (2013.01); C07D 233/58 (2013.01); C07D 401/14 (2013.01); C07D 403/04 (2013.01); C07D 405/04 (2013.01); C07D 405/14 (2013.01); C07D 409/04 (2013.01); C07D 409/14 (2013.01); C07D 413/04 (2013.01); C07D 413/14 (2013.01); C07D 417/04 (2013.01); C07D 417/14 (2013.01); C07F 15/0033 (2013.01); C07F 15/0086 (2013.01); C09K 11/06 (2013.01); H01L 51/0087 (2013.01); H05B 33/14 (2013.01); C09K 2211/1007 (2013.01); C09K 2211/1011 (2013.01); C09K 2211/1029 (2013.01); C09K 2211/1033 (2013.01); C09K 2211/1037 (2013.01); C09K 2211/1044 (2013.01); C09K 2211/1088 (2013.01); C09K 2211/1092 (2013.01); C09K 2211/185 (2013.01); C09K 2211/186 (2013.01); H01L 51/006 (2013.01); H01L 51/0042 (2013.01); H01L 51/0059 (2013.01); H01L 51/0069 (2013.01); H01L 51/0071 (2013.01); H01L 51/0081 (2013.01); H01L 51/5016 (2013.01); H01L 2251/308 (2013.01)

(58) Field of Classification Search
None
See application file for complete search history.

(56) References Cited

U.S. PATENT DOCUMENTS

| | | |
|---|---|---|
| 4,914,476 A | 4/1990 | Nishitsuji et al. |
| 5,061,569 A | 10/1991 | Vanlyke et al. |
| 5,905,925 A | 5/1999 | Kawabata et al. |
| 6,097,147 A | 8/2000 | Baldo et al. |
| 2003/0059647 A1 | 3/2003 | Thompson et al. |
| 2003/0068536 A1 | 4/2003 | Tsuboyama et al. |
| 2004/0091738 A1 | 5/2004 | Psai et al. |
| 2004/0137268 A1* | 7/2004 | Igarashi et al. ............ 428/690 |
| 2005/0013626 A1 | 1/2005 | Satoh et al. |
| 2005/0135827 A1 | 6/2005 | Akita et al. |
| 2005/0249970 A1 | 11/2005 | Suzuri et al. |
| 2006/0073360 A1* | 4/2006 | Ise et al. ................ 428/690 |

FOREIGN PATENT DOCUMENTS

| | | |
|---|---|---|
| JP | 63228177 A | 9/1988 |
| JP | 63264692 A | 11/1988 |
| JP | 1074586 A | 3/1989 |

(Continued)

OTHER PUBLICATIONS

Machine translation of JP2003-272861. Date of publication: Sep. 26, 2003.*

(Continued)

Primary Examiner — Andrew K Bohaty
(74) Attorney, Agent, or Firm — Cantor Colburn LLP

(57) ABSTRACT

This invention provides an organic EL element, which can control luminescence wavelength, exhibits high luminescence efficiency, and has a prolonged emission life, and a lighting equipment and a display device. They can be realized by an organic electroluminescent element material characterized by a metal complex having a structure represented by the following general formula (A) as a partial structure.

6 Claims, 2 Drawing Sheets

(56) References Cited

FOREIGN PATENT DOCUMENTS

| | | | |
|---|---|---|---|
| JP | 3255190 A | 11/1991 |
| JP | 4308688 A | 10/1992 |
| JP | 5142884 A | 6/1993 |
| JP | 6325871 A | 11/1994 |
| JP | 8288069 A | 11/1996 |
| JP | 9017574 A | 1/1997 |
| JP | 9045479 A | 2/1997 |
| JP | 9260062 A | 10/1997 |
| JP | 11204258 A | 7/1999 |
| JP | 11204359 A | 7/1999 |
| JP | 3093796 B2 | 10/2000 |
| JP | 2001181616 A | 7/2001 |
| JP | 2001181617 A | 7/2001 |
| JP | 2001247859 A | 9/2001 |
| JP | 2001257076 A | 9/2001 |
| JP | 2001313178 A | 11/2001 |
| JP | 2001313179 A | 11/2001 |
| JP | 2001319779 A | 11/2001 |
| JP | 2001319780 A | 11/2001 |
| JP | 2001345183 A | 12/2001 |
| JP | 2001357977 A | 12/2001 |
| JP | 2002008860 A | 1/2002 |
| JP | 2002015871 A | 1/2002 |
| JP | 2002034894 A | 2/2002 |
| JP | 2002043056 A | 2/2002 |
| JP | 2002050483 A | 2/2002 |
| JP | 2002050484 A | 2/2002 |
| JP | 2002062824 A | 2/2002 |
| JP | 2002075645 A | 3/2002 |
| JP | 2002083684 A | 3/2002 |
| JP | 2002100474 A | 4/2002 |
| JP | 2002100476 A | 4/2002 |
| JP | 2002105445 A | 4/2002 |
| JP | 2002117978 A | 4/2002 |
| JP | 2002132086 A | 5/2002 |
| JP | 2002141173 A | 5/2002 |
| JP | 2002170684 A | 6/2002 |
| JP | 2002173674 A | 6/2002 |
| JP | 2002175884 A | 6/2002 |
| JP | 2002203678 A | 7/2002 |
| JP | 2002203679 A | 7/2002 |
| JP | 2002203683 A | 7/2002 |
| JP | 2002226495 A | 8/2002 |
| JP | 2002231453 A | 8/2002 |
| JP | 2002234888 A | 8/2002 |
| JP | 2002235076 A | 8/2002 |
| JP | 2002241751 A | 8/2002 |
| JP | 2002525808 A | 8/2002 |
| JP | 2002525833 A | 8/2002 |
| JP | 2002255934 A | 9/2002 |
| JP | 2002260861 A | 9/2002 |
| JP | 2002280178 A | 9/2002 |
| JP | 2002280179 A | 9/2002 |
| JP | 2002280180 A | 9/2002 |
| JP | 2002280183 A | 9/2002 |
| JP | 2002284582 A | 10/2002 |
| JP | 2002299060 A | 10/2002 |
| JP | 2002302516 A | 10/2002 |
| JP | 2002302671 A | 10/2002 |
| JP | 2002305083 A | 10/2002 |
| JP | 2002305084 A | 10/2002 |
| JP | 2002308837 A | 10/2002 |
| JP | 2002308855 A | 10/2002 |
| JP | 2002319491 A | 10/2002 |
| JP | 2002324679 A | 11/2002 |
| JP | 2002332291 A | 11/2002 |
| JP | 2002332292 A | 11/2002 |
| JP | 2002334786 A | 11/2002 |
| JP | 2002334787 A | 11/2002 |
| JP | 2002334788 A | 11/2002 |
| JP | 2002334789 A | 11/2002 |
| JP | 2002338579 A | 11/2002 |
| JP | 2002338588 A | 11/2002 |
| JP | 2002343568 A | 11/2002 |
| JP | 2002343572 A | 11/2002 |
| JP | 2002540572 A | 11/2002 |
| JP | 2002352957 A | 12/2002 |
| JP | 2002352960 A | 12/2002 |
| JP | 2002359082 A | 12/2002 |
| JP | 2002363227 A | 12/2002 |
| JP | 2002363552 A | 12/2002 |
| JP | 2003003165 A | 1/2003 |
| JP | 2003007469 A | 1/2003 |
| JP | 2003007471 A | 1/2003 |
| JP | 2003027048 A | 1/2003 |
| JP | 2003031366 A | 1/2003 |
| JP | 2003123982 A | 4/2003 |
| JP | 2003146996 A | 5/2003 |
| JP | 2003192691 A | 7/2003 |
| JP | 2003252888 A | 9/2003 |
| JP | 2003272861 A * | 9/2003 |
| JP | 2005068110 | 3/2005 |
| JP | 2005129478 A | 5/2005 |
| JP | 2006028101 A | 2/2006 |
| JP | 2006083353 A | 3/2006 |
| JP | 2006120762 A | 5/2006 |
| JP | 2006120905 A | 5/2006 |
| WO | 0070655 A2 | 11/2000 |
| WO | 0193642 A1 | 12/2001 |
| WO | 0215645 A1 | 2/2002 |
| WO | 2004016711 A1 | 2/2004 |
| WO | 2004026886 | 4/2004 |
| WO | 2004053019 A1 | 6/2004 |
| WO | 2004095889 A1 | 11/2004 |

OTHER PUBLICATIONS

European Search Report for Application No. 08150207.2-1240 mailed Jul. 1, 2008.with English translation.
Notice of Reasons for Refusal for Japanese Patent Application No. 2007-523378, drafted Apr. 27, 2012, with English translation.

* cited by examiner

LIGHT

LIGHT

ORGANIC ELECTROLUMINESCENT ELEMENT MATERIAL, ORGANIC ELECTROLUMINESCENT ELEMENT, DISPLAY DEVICE, AND LIGHTING DEVICE

CROSS REFERENCE TO RELATED APPLICATIONS

The present application is a continuation application of U.S. patent application Ser. No. 11/994,046, filed on Dec. 27, 2007, the entire contents of which are incorporated herein by reference and priority to which is hereby claimed. application Ser. No. 11/994,046 is the U.S. National stage of application No. PCT/JP2006/311260, filed Jun. 6, 2006. Priority under 35 U.S.C. §119(a) and 35 U.S.C. §365(b) is hereby claimed from Japanese Application No. 2005-193697, filed Jul. 1, 2005, the disclosure of which is also incorporated herein by reference.

TECHNICAL FIELD

The present invention relates to an organic electroluminescent element material, an organic electroluminescent element, a display device and a lighting device.

BACKGROUND

Conventionally, an emission type electronic display device includes an electroluminescence display (hereinafter, referred to as an ELD). A constituent element of ELD includes such as an inorganic electroluminescent element and an organic electroluminescent element (hereinafter, referred to as an organic EL element). An inorganic electroluminescent element has been utilized as a flat light source, however, requires a high voltage of alternating current to operate an emission element. An organic electroluminescent element is an element provided with a constitution comprising an emission layer containing a emitting substance being sandwiched with a cathode and an anode, and an exciton is generated by an electron and a positive hole being injected into the emission layer to be recombined, resulting emission utilizing light release (fluorescence•phosphorescence) at the time of deactivation of said exciton; the emission is possible at a voltage of approximately a few to a few tens volts, and an organic electroluminescent element is attracting attention with respect to such as superior viewing angle and high visual recognition due to a self-emission type as well as space saving and portability due to a completely solid element of a thin layer type.

However, in an organic electroluminescence in view of the future practical application, desired has been development of an organic EL element which efficiently emits at a high luminance with a low electric consumption.

In Japanese Patent No. 3093796, a slight amount of a fluorescent substance has been doped in a stilbene derivative, distyrylarylene derivative or a tristyrylarylene derivative, to achieve improved emission luminance and a prolonged life of an element.

Further, there are known such as an element having an organic emission layer comprising a 8-hydroxyquinoline aluminum complex as a host compound which is doped with a slight amount of a fluorescent substance (for example, JP-A 63-264692 (hereinafter, JP-A refers to Japanese Patent Publication Open to Public Inspection No.)) and an element having an organic emission layer comprising a 8-hydroxyquinoline aluminum complex as a host compound which is doped with quinacridone type dye (for example, JP-A 3-255190).

In the case of utilizing emission from an excited singlet as described above, since a generation ratio of a singlet exciton to a triplet exciton is 1/3, that is, a generation probability of an emitting exciton species is 25% and a light taking out efficiency is approximately 20%, the limit of a quantum efficiency ($\eta$ext) of taking out is said to be 5%.

However, since an organic EL element which utilizes phosphorescence from an excited triplet has been reported from Princeton University (M. A. Baldo et al., Nature vol. 395, pp. 151-154 (1998)), researches on materials exhibiting phosphorescence at room temperature have come to be active.

For example, it is also disclosed in A. Baldo et al., Nature, vol. 403, No. 17, pp. 750-753 (2000), and U.S. Pat. No. 6,097,147.

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application.

For example, in such as S. Lamansky et al., J. Am. Chem. Soc., vol. 123, p. 4304 (2001), many compounds mainly belonging to heavy metal complexes such as iridium complexes have been synthesized and studied.

Further, in aforesaid, A. Baldo et al., Nature, vol. 403, No. 17, pp. 750-753 (2000), utilization of tris(2-phenylpyridine) iridium as a dopant has been studied.

In addition to these, M. E. Tompson et al., at The 10th International Workshops on Inorganic and Organic Electroluminescence (EL'00, Hamamatsu), have studied to utilize $L_2$Ir (acac) such as $(ppy)_2$Ir(acac) as a dopant, Moon-Jae Youn. Og., Tetsuo Tsutsui et al., also at The 10th International Workshops on Inorganic and Organic Electroluminescence (EL'00, Hamamatsu), have studied utilization of such as tris (2-(p-tolyl)pyridine)iridium (Ir(ptpy)$_3$) and tris(benzo[h] quinoline)iridium (Ir(bzq)$_3$) (herein, these metal complexes are generally referred to as orthometalated iridium complexes.).

Further, in also the aforesaid, S. Lamansky et al., J. Am. Chem. Soc., vol. 123, p. 4304 (2001), studies have been carried out to prepare an element utilizing various types of iridium complexes.

Further, to obtain high emission efficiency, Ikai et al., at The 10th International Workshops on Inorganic and Organic Electroluminescence (EL'00, Hamamatsu) utilized a hole transporting compound as a host of a phosphorescent compound. Further, M. E. Tompson et al. utilized various types of electron transporting materials as a host of a phosphorescent compound doped with a new iridium complex.

An orthometalated complex provided with platinum instead of iridium as a center metal is also attracting attention. With respect to these types of complexes, many examples having a characteristic ligand are known (for example, refer to Patent Documents 1-5 and Non-Patent Document 1.).

In any case, emission luminance and emission efficiency are significantly improved compared to conventional elements because the emitting light arises from phosphorescence, however, there has been a problem of a poor emission life of the element compared to conventional elements. It is hard to achieve an emission of a short wavelength and an improvement of an emission life of the element for a phosphorescent emission material provided with a high efficiency. At present state, it cannot be achieved a level of a practical use.

With respect to shortening of emission wavelength, heretofore, there have been known introduction of an electron attracting group such as a fluorine atom, a trifluoromethyl group, or a cyano group as a substituent group into phenylpyridine, and introduction of a ligand of such as picolinic acid or of a pyrazabole type. However, when an emission wavelength is shortened to achieve blue color by utilizing these substitution effects, a high efficiency may be achieved while emission life will be greatly deteriorated, which requires further improvement to overcome the trade-off relationship.

There are known some iridium complexes containing a ligand having a specific partial structure combining two carbon atoms of two five membered ring. However, in the disclosed compounds, at least one of the five membered rings is condensed with other ring. In addition, there are disclosed only the use for a red emission element (refer to Patent Document 11.)

[Patent Document 1] JP-A 2002-332291
[Patent Document 2] JP-A 2002-332292
[Patent Document 3] JP-A 2002-338588
[Patent Document 4] JP-A 2002-226495
[Patent Document 5] JP-A 2002-234894
[Patent Document 6] WO 02/15645
[Patent Document 7] JP-A 2003-123982
[Patent Document 8] JP-A 2002-117978
[Patent Document 9] JP-A 2003-146996
[Patent Document 10] WO 04/016711
[Patent Document 11] JP-A 2003-252888
[Non-patent Document 1] Inorganic Chemistry, 41 (12), 3055-3066 (2002)
[Non-patent Document 2] Applied Physics Letters, 79, 2082 (2001)
[Non-patent Document 3] Applied Physics Letters, 83, 3818 (2003)
[Non-patent Document 4] New Journal of Chemistry, 26, 1171 (2002)

DISCLOSURE OF THE INVENTION

Problems to be Solved by the Invention

This invention has been made in view of these problems, and an object of this invention is to provide an organic EL element material with a controlled emission wavelength which have high emission efficiency and long emission life, a lighting device and a display device by utilizing said element material.

Means to Solve the Problems

An object of the present invention described above has been achieved by the following constitutions 1-15.
(1) An organic electroluminescent element material characterized by a metal complex having a structure represented by Formula (A) as a partial structure.

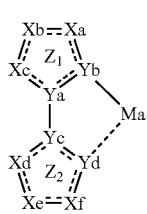

Formula (A)

wherein Xa, Xb, Xc, Xd, Xe, and Xf each represent a carbon atom, CRa, a nitrogen atom, NRb, an oxygen atom, or a sulfur atom, but at least one of them represents CRa. Ya, Yb, and Yc each represent a carbon atom or a nitrogen atom and Yd represents a nitrogen atom. When Ya and Yb represent the same atom, Yc does not represent a nitrogen atom. Ra and Rb represent a hydrogen atom or a substituent, but at least one of Ra represents an aromatic hydrocarbon ring group or an aromatic heterocyclic ring group. Ma represents a metal of the 8th-10th groups of the periodic table of elements. Rings Z1 and Z2 each represent a single five-membered ring, and the bonds to form each of the rings $Z_1$ and $Z_2$ each represent a single bond or a double bond, the rings $Z_1$ and $Z_2$ each being a single ring.
(2) The organic electroluminescent element material described in item (1) characterized by a metal complex having a structure represented by Formula (1) as a partial structure.

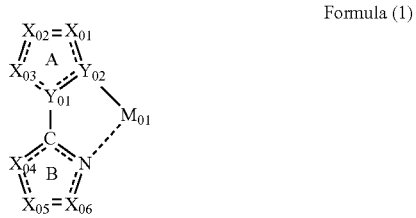

Formula (1)

wherein $X_{01}$, $X_{02}$, $X_{03}$, $X_{04}$, $X_{05}$, and $X_{06}$ each represent $CR_{01}$, a nitrogen atom, $NR_{02}$, an oxygen atom, or a sulfur atom, but at least one of them represents $CR_{01}$. $Y_{01}$ and $Y_{02}$ each represent a carbon atom or a nitrogen atom. $R_{01}$ and $R_{02}$ each represent a hydrogen atom or a substituent, but at least one of $R_{01}$ represents an aromatic hydrocarbon ring group or an aromatic heterocyclic ring group. $M_{01}$ represents a transition metal element of the 8th-10th groups of the periodic table of elements. Rings A and B each represent a single five-membered ring, and the bonds to form each of the rings A and B represent a single bond or a double bond.
(3) The organic electroluminescent element material described in item (1) characterized by a metal complex having a structure represented by Formula (2) as a partial structure.

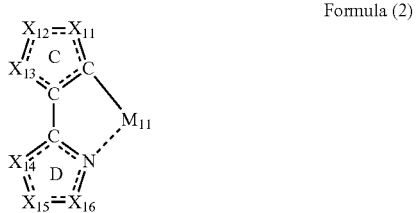

Formula (2)

wherein $X_{11}$, $X_{12}$, $X_{13}$, $X_{14}$, $X_{15}$, and $X_{16}$ each represent $CR_{11}$, a nitrogen atom, $NR_{12}$, an oxygen atom, or a sulfur atom, but at least one of them represents $CR_{11}$. $R_{11}$ and $R_{12}$ each represent a hydrogen atom or a substituent, but at least one of $R_{11}$ represents an aromatic hydrocarbon ring group or an aromatic heterocyclic ring group. $M_{11}$ represents a transition metal element of the 8th-10th groups of the periodic table of elements. Rings C and D each represent a single five-membered ring, and the bonds to form each of the rings C and D each represent a single bond or a double bond.
(4) The organic electroluminescent element material described in item (1) characterized by a metal complex having a structure represented by Formula (3) as a partial structure.

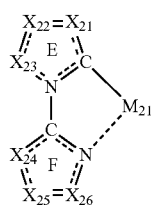

Formula (3)

wherein $X_{21}$, $X_{22}$, $X_{23}$, $X_{24}$, $X_{25}$, and $X_{26}$ each represent $CR_{21}$, a nitrogen atom, $NR_{22}$, an oxygen atom, or a sulfur atom, but at least one of them represents $CR_{21}$. $R_{21}$ and $R_{22}$ each represent a hydrogen atom or a substituent, but at least one of $R_{21}$ represents an aromatic hydrocarbon ring group or an aromatic heterocyclic ring group. $M_{21}$ represents a transition metal element of the 8th-10th groups of the periodic table of elements. Rings E and F each represent a single five-membered ring, and the bonds to form each of the rings E and F represent a single bond or a double bond.

(5) The organic electroluminescent element material described in item (1) characterized by a metal complex having a structure represented by Formula (4) as a partial structure.

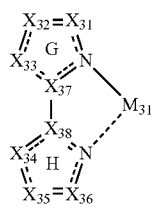

Formula (4)

wherein $X_{31}$, $X_{32}$, $X_{33}$, $X_{34}$, $X_{35}$, and $X_{36}$ each represent $CR_{31}$, a nitrogen atom, $NR_{32}$, an oxygen atom, or a sulfur atom, but at least one of them represents $CR_{31}$. $X_{37}$ and $X_{38}$ each represent a carbon atom or a nitrogen atom. $R_{31}$ and $R_{32}$ each represent a hydrogen atom or a substituent, but at least one of $R_{31}$ represents an aromatic hydrocarbon ring group or an aromatic heterocyclic ring group. $M_{31}$ represents a transition metal element of the 8th-10th groups of the periodic table of elements. Rings G and H each represent a single five-membered ring, and the bonds to form each of the rings G and H represent a single bond or a double bond.

(6) The organic electroluminescent element material described in item (1), wherein Ma in Formula (A) is iridium or platinum.

(7) The organic electroluminescent element material described in item (3), wherein $M_{01}$ in Formula (1) is iridium or platinum.

(8) The organic electroluminescent element material described in item (3), wherein $M_{11}$ in Formula (2) is iridium or platinum.

(9) The organic electroluminescent element material described in item (4), wherein $M_{21}$ in Formula (3) is iridium or platinum.

(10) The organic electroluminescent element material described in item (5), wherein $M_{31}$ in Formula (4) is iridium or platinum.

(11) An organic electroluminescent element comprising any one of the organic electroluminescent element materials described in items (1)-(10).

(12) An organic electroluminescent element comprising an emission layer as a constituting layer of the element, wherein the emission layer comprises any one of the organic electroluminescent element materials described in items (1)-(10).

(13) An organic electroluminescent element comprising an electron inhibition layer as a constituting layer of the element, wherein the electron inhibition layer comprises any one of the organic electroluminescent element materials described in items (1)-(10).

(14) The organic electroluminescent element of any one of the above-described items (11)-(13), comprising an emission layer as a constituting layer of the element, the emission layer containing:
a carboline derivative; or
a condensed ring compound having a structure derived from carboline, wherein at least one of carbon atoms of a hydrocarbon ring in a carboline ring is substituted with a nitrogen atom.

(15) The organic electroluminescent element of any one of the above-described items (11)-(14), comprising a positive hole inhibition layer as a constituting layer of the element, the positive hole inhibition layer containing:
a carboline derivative; or
a condensed ring compound having a structure derived from carboline, wherein at least one of carbon atoms of a hydrocarbon ring in a carboline ring is substituted with a nitrogen atom.

(16) A display device comprising any one of the organic electroluminescent elements described in items (11)-(15).

(17) A lighting device comprising any one of the organic electroluminescent elements described in items (11)-(15).

Effects of the Invention

This invention has been able to provide an organic EL element material for and an organic EL element, and it has been achieved to provide an organic EL element, a lighting device and a display device having high emission efficiency and long emission life utilizing said organic EL element material.

Figure 1:
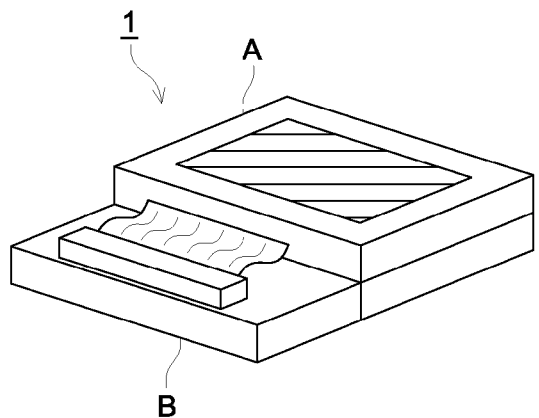
FIG. 1 is a schematic drawing to show an example of a display device constituted of an organic EL element.

DESCRIPTION OF SYMBOLS 1 display
3 pixel
5 scanning line
6 data line
7 electrical power line
10 organic EL element
11 switching transistor
12 operating transistor
13 capacitor
A display section
B control section 107 glass substrate having a transparent electrode
106 organic EL layer
105 cathode
102 glass cover
108 nitrogen gas
109 desiccant

BEST MODES TO CARRY OUT THE INVENTION

In the organic EL element material of the present invention, molecular designing of an organic EL element material for use in an organic EL element has been realized via the embodiment set forth by any one of items (1)-(8). Further, by use of the organic EL element material, there has been provided an organic EL element exhibiting high emission efficiency and having a prolonged emission life, lighting equipment, and a display device.

Each of the constituent elements of the present invention will now be detailed successively.

<Metal Complex Having a Structure Represented by any One of Formulas (A) and (1)-(4) as a Partial Structure>

A metal complex relevant to the organic EL element material of the present invention is described.

The inventors of the present invention have conducted diligent investigation on the above problems and made the following findings: emission efficiency was significantly enhanced employing an organic EL element containing a metal complex material having a specific partial structure as the organic EL element material, wherein as the ligand of the metal complex, the mother nucleus of a commonly used phenylpyridine (being structured of two six-membered rings joining each other via a carbon-carbon bond) was coordinated to the mother nucleus having a structure in which "the five-membered aromatic heterocyclic rings", represented by Formulas (A) and (1)-(4), joined each via a carbon-carbon bond or a carbon-nitrogen bond.

However, such a ligand, in which two five-membered rings each join via a carbon-carbon bond or a carbon-nitrogen bond, tends to be electron-deficient as a whole, resulting in the problem in that the stability of a compound is likely to decrease, and therefore in order to enhance the stability of the compound, a breakthrough in molecular designing has been further demanded.

The inventors of the present invention have found that, by introducing an aromatic hydrocarbon ring or an aromatic heterocyclic ring as a substituent of the ligand having a structure in which two five-membered rings each join via a carbon-carbon bond or a carbon-nitrogen bond in such a manner as in the metal complex of the present invention, an emission life was able to be prolonged which had been a problem of the organic EL element produced employing an organic EL element material exhibiting an emission wavelength controlled to be in the short wavelength side only via a conventional blue metal complex, specifically via an electron-attracting group, whereby compatibility of emission efficiency and an emission life has been realized.

Specifically, in molecular designing a phosphorescence-emitting blue dopant used preferably as a blue light-emitting dopant, molecular designing via a viewpoint different from the conventional one has been realized, and at the same time a greatly prolonged emission life of the organic EL element has been achieved.

Further, the following findings have been made: even when the ligand has a structure in which two five-membered rings each join via a carbon-carbon bond or a carbon-nitrogen bond, a long emission wavelength might be realized depending on the structure of the ligand, and also in molecular designing for adding a function to enable the emission wavelength of the metal complex to be in the long wavelength region, an appropriate partial structure was able to be selected by employing the partial structure of the present invention represented by Formulas (A) and (1)-(4) or a partial structure expressed as a tautomer of each partial structure represented by Formulas (A) and (1)-(4) as a starting material for designing the original skeleton.

(Ligand)

The metal complex of the present invention is characterized by having one of the partial structure represented by Formulas (A) and (1)-(4) and a partial structure expressed as a tautomer of each partial structure represented by Formulas (A) and (1)-(4) (specifically by having the partial structure as a coordination structure), wherein any of the metal complex may be composed of only the partial structure represented by Formulas (A) and (1)-(4) or a partial structure expressed as a tautomer of each partial structure represented by Formulas (A) and (1)-(4), and also, as the ligand, any of the metal complex may have a ligand (also called a coordination compound), if necessary, which is known among persons skilled in the art as a so called ligand used to prepare metal complexes known in the art.

In view of achieving preferable results in desired effects of the present invention, the ligand in complexes is composed of 1 or 2 types, but is preferably composed of only one type.

Ligands employed in conventional metal complexes known in the art include various types. Examples include ligands (for example, halogen ligands, being preferably a chlorine ligand, and nitrogen containing heterocyclic ligands such as bipyridyl or phenanthroline, and diketone ligands) described, for example, in H. Yersin, "Photochemistry and Photophysics of Coordination Compounds" Springer-Verlag Co., published in 1987, and in Akio Yamamoto, "Yuki Kinzoku Kagaku—Kiso to Oyo—(Organic Metal Chemistry—Bases and Applications—)" Shokabo Sha, published in 1982.

(Transition Metal Elements of Groups 8-10 of the Periodic Table of Elements)

Employed as a metal used to form the metal complexes containing a partial structure represented by one of Formulas (A), and (1)-(4) (more definitely, containing as a ligand) according to the present invention, the transition metal elements (also simply referred to as transition metals) of Groups 8-10 of the periodic table. Of these, iridium and platinum are listed as a preferable transition metal element.

The layer in which the metal complexes containing a partial structure represented by one of Formulas (A), and (1)-(4) is preferably an emission layer and/or an electron inhibition layer. Further, when incorporated in the emission layer, by employing them as an emission dopant in the emission layer ("an emission dopant" will be explained later), it is possible to achieve an increase in the quantum efficiency (to realize high luminance) to be taken out and the extension of luminescent lifetime of the organic EL elements of the present invention.

Further, by employing such organic EL element materials, it became possible to provide organic EL elements which exhibit high luminescent efficiency and long luminescent lifetime, a lighting device and a display device.

Each of the constituting components according to the present invention will now be successively detailed.

Metal complexes which are organic EL element materials of the present invention will be described first.

Preferred as a layer incorporating the metal complexes containing a partial structure represented by one of Formulas (A) and (1)-(4) according to the present invention is an emission layer and/or an electron inhibition layer. Further, when incorporated in the emission layer, by employing them as an emission dopant in the emission layer, it is possible to achieve an increase in the quantum efficiency (to realize high luminance) to be taken out and the extension of luminescent lifetime of the organic EL elements of the present invention.

The partial structures represented by Formulas (A) and (1)-(4) and contained in the metal complexes of the present invention will be described next.

<<A Partial Structure Represented by Formula (A)>>

In Formula (A), Xa, Xb, Xc, Xd, Xe, and Xf each represents a carbon atom, CRa, a nitrogen atom, NRb, an oxygen atom or a sulfur atom. At least one of them represents CRa.

Examples of substituents represented by Xa, Xb, Xc, Xd, Xe, and Xf; Ra of CRa; and Rb of NRb in Formula (A) are as follows. Examples of such a substituent include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group), a cycloalkyl group (for example, a cyclopentyl group and a cyclohexyl group), an alkenyl group (for example, a vinyl group and an allyl group), an alkynyl group (for example, an ethynyl group and a propargyl group), an aromatic hydrocarbon ring group (also called an aromatic carbon ring group or an aryl group such as a phenyl group, a p-chlorophenyl group, a mesityl group, a tolyl group, a xylyl group, a naphthyl group, an anthryl group, an azulenyl group, an acenaphthenyl group, fluorenyl group, a phenanthryl group, an indenyl group, a pyrenyl group, or a biphenyl group), an aromatic heterocyclic group (for example, a pyridyl group, a pyrimidinyl group, a furyl group, a pyrrolyl group, an imidazolyl group, a benzimidazolyl group, a pyrazolyl group, a piradinyl group, a triazolyl group (for example, a 1,2,4-triazole-1-yl group and a 1,2,3-triazole-1-yl group), an oxazolyl group, a benzoxazolyl group, a triazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolynyl group, a diazacarbazoyl group (which shows that one of the carbon atoms which constitute a carboline ring of the above carbolinyl group is replaced with a nitrogen atom), a quinoxythalinyl group, a pyridazinyl group, a triazinyl group, a quinazolinyl group, a phthalazinyl group), a heterocyclic group (for example, a pyrrolidinyl group, an imidazolidyl group, a morpholyl group, and an oxazolidyl group), an alkoxy group (for example, a methoxy group, an ethoxy group, a propyloxy group, a pentyloxy group, a hexyloxy group, an octyloxy group, and a dodecyloxy group), a cycloalkoxy group (for example, a cyclopentyloxy group and a cyclohexyloxy group), an aryloxy group (for example, a phenoxy group and a naphthyloxy group), an alkylthio group (for example, a methylthio group, an ethylthio group, a propylthio group, a pentylthio group, a hexylthio group, an octylthio group, and a dodecylthio group), a cycloalkylthio group (for example, a cyclopentylthio group and a cyclohexylthio group), an arylthio group (for example, a phenylthio group and a naphthylthio group), an alkoxycarbonyl group (for example, a methyloxycarbonyl group, an ethyloxycarbonyl group, a butyloxycarbonyl group, an octyloxycarbonyl group, and a dodecyloxycarbonyl group), an aryloxycarbonyl group (for example, a phenyloxycarbonyl group and a naphthyloxycarbonyl group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group), an acyloxy group (for example, an acetyloxy group, an ethylcarbonyloxy group, a butylcarbonyloxy group, an octylcarbonyloxy group, a dodecylcarbonyloxy group, and a phenylcarbonyloxy group), an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group), an ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group), a sulfinyl group (for example, a methylsulfinyl group, an ethylsulfinyl group, a butylsulfinyl group, a cyclohexylsulfinyl group, a 2-ethylhexylsulfinyl group, a docecylsulfinyl group, a phenylsulfinyl group, a naphthylsulfinyl group, and a 2-pyridylsulfinyl group), an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group), an arylsulfonyl group or a heteroarylsulfonyl group (for example, a phenylsulfonyl group, a naphthylsulfonyl group, and a 2-pyridylsulfonyl group), an amino group (for example, an amino group, an ethylamino group, a dimethylamino group, a butylamino group, a cyclopentylamino group, a 2-ethylhexylamino group, a dodecylamino group, an anilino group, a cyclopentylamino group, a 2-ethylhexylamino group, a dodecylamino group, an anilino group, a naphthylamino group, and a 2-pyridylamino group), a halogen atom (for example, a fluorine atom, a chlorine atom, and a bromine atom), a fluorinated hydrocarbon group (for example, a fluoromethyl group, a trifluoromethyl group, a pentafluoroethyl group, and a pentafluorophenyl group), a cyano group, a nitro group, a hydroxyl group, a mercapto group, and a silyl group (for example, a trimethylsilyl group, a triisopropylsilyl group, a triphenylsilyl group, and a phenyldiethylsilyl group).

These substituents may be substituted with the above substituents. Further, these substituents may be bound together to form a ring.

Ra represents a hydrogen atom or a substituent. The substituent is a group similar to each substituent represented by Ra and Rb, but at least one of Ra and Rb is an aromatic hydrocarbon ring group or an aromatic heterocyclic ring group. As the aromatic hydrocarbon ring group or the aromatic heterocyclic ring group, a phenyl group, thienyl group, pyridyl group, imidazolyl group, and pyrazolyl group are preferable, but of these, a phenyl group is more preferably utilized.

Ya, Yb, and Yc each represent a carbon atom or a nitrogen atom, and Yd represents a nitrogen atom. When Ya and Yb represent the same atom, Yc does not represent a nitrogen atom.

In Formula (A), Ma represents a transition metal element of the 8th-10th groups of the periodic table of elements, but of these, iridium and platinum are preferably utilized.

In Formula (A), the rings $Z_1$ and $Z_2$ each represent a single five-membered ring, and the bonds to each form the rings $Z_1$ and $Z_2$ are a single bond or a double bond.

Examples of a carbon ring of the single five-membered ring utilized as the ring $Z_1$ include a cyclopentane ring and a cyclopentadiene ring.

As a heterocyclic ring of the single five-membered ring utilized as the ring $Z_1$, there are preferably utilized a furan ring, thiophene ring, selenophene ring, tellurophene ring, oxazole ring, isoxazole ring, oxadine ring, pyrrole ring, pyrazole ring, oxadiazole ring, triazole ring, imidazole ring, pyrazole ring, triazole ring, isothiazole ring, pyrrolidine ring, pyrazolidine ring, imidazolidine ring, isoxazolidine ring, and isothiazolidine ring.

The single five-membered ring utilized as the ring $Z_2$ is synonymous with the heterocyclic ring of the single five-membered ring described as the ring $Z_1$.

The single five-membered rings each formed with the rings $Z_1$ and $Z_2$ in Formula (A) incorporate Xa, Xb, Xc, Xd, Xe, and Xf, which may further have a substituent each represented by Ra or Rb contained in CRa or NRb.

Further, the bonds to each form the rings $Z_1$ and $Z_2$ are a single bond or a double bond, but may also be a bond with a bond order such as 1.5 positioned between the single bond and the double bond.

<A Partial Structure Represented by Formula (1)>

In Formula (1), at least one of $X_{01}$, $X_{02}$, $X_{03}$, $X_{04}$, $X_{05}$, and $X_{06}$ is represented by $CR_{01}$.

Examples of substituents represented by $X_{01}$, $X_{02}$, $X_{03}$, $X_{04}$, $X_{05}$, $X_{06}$; $R_{01}$ of $CR_{01}$; and $R_{02}$ of $NR_{02}$ in Formula (1) are as follows. Examples of such a substituent include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group), a cycloalkyl group (for example, a cyclopentyl group and a cyclohexyl group), an alkenyl group (for example, a vinyl group and an allyl group), an alkynyl group (for example, an ethynyl group and a propargyl group), an aromatic hydrocarbon ring group (also called an aromatic carbon ring group or an aryl group such as a phenyl group, a p-chlorophenyl group, a mesityl group, a tolyl group, a xylyl group, a naphthyl group, an anthryl group, an azulenyl group, an acenaphthenyl group, fluorenyl group, a phenanthryl group, an indenyl group, a pyrenyl group, or a biphenyl group), an aromatic heterocyclic group (for example, a pyridyl group, a pyrimidinyl group, a furyl group, a pyrrolyl group, an imidazolyl group, a benzimidazolyl group, a pyrazolyl group, a piradinyl group, a triazolyl group (for example, a 1,2,4-triazole-1-yl group and a 1,2,3-triazole-1-yl group), an oxazolyl group, a benzoxazolyl group, a triazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolynyl group, a diazacarbazoyl group (which shows that one of the carbon atoms which constitute a carboline ring of the above carbolinyl group is replaced with a nitrogen atom), a quinoxythalinyl group, a pyridazinyl group, a triazinyl group, a quinazolinyl group, a phthalazinyl group), a heterocyclic group (for example, a pyrrolidinyl group, an imidazolidyl group, a morpholyl group, and an oxazolidyl group), an alkoxy group (for example, a methoxy group, an ethoxy group, a propyloxy group, a pentyloxy group, a hexyloxy group, an octyloxy group, and a dodecyloxy group), a cycloalkoxy group (for example, a cyclopentyloxy group and a cyclohexyloxy group), an aryloxy group (for example, a phenoxy group and a naphthyloxy group), an alkylthio group (for example, a methylthio group, an ethylthio group, a propylthio group, a pentylthio group, a hexylthio group, an octylthio group, and a dodecylthio group), a cycloalkylthio group (for example, a cyclopentylthio group and a cyclohexylthio group), an arylthio group (for example, a phenylthio group and a naphthylthio group), an alkoxycarbonyl group (for example, a methyloxycarbonyl group, an ethyloxycarbonyl group, a butyloxycarbonyl group, an octyloxycarbonyl group, and a dodecyloxycarbonyl group), an aryloxycarbonyl group (for example, a phenyloxycarbonyl group and a naphthyloxycarbonyl group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group), an acyloxy group (for example, an acetyloxy group, an ethylcarbonyloxy group, a butylcarbonyloxy group, an octylcarbonyloxy group, a dodecylcarbonyloxy group, and a phenylcarbonyloxy group), an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group), an ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group), a sulfinyl group (for example, a methylsulfinyl group, an ethylsulfinyl group, a butylsulfinyl group, a cyclohexylsulfinyl group, a 2-ethylhexylsulfinyl group, a docecylsulfinyl group, a phenylsulfinyl group, a naphthylsulfinyl group, and a 2-pyridylsulfinyl group), an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group), an arylsulfonyl group or a heteroarylsulfonyl group (for example, a phenylsulfonyl group, a naphthylsulfonyl group, and a 2-pyridylsulfonyl group), an amino group (for example, an amino group, an ethylamino group, a dimethylamino group, a butylamino group, a cyclopentylamino group, a 2-ethylhexylamino group, a dodecylamino group, an anilino group, a cyclopentylamino group, a 2-ethylhexylamino group, a dodecylamino group, an anilino group, a naphthylamino group, and a 2-pyridylamino group), a halogen atom (for example, a fluorine atom, a chlorine atom, and a bromine atom), a fluorinated hydrocarbon group (for example, a fluoromethyl group, a trifluoromethyl group, a pentafluoroethyl group, and a pentafluorophenyl group), a cyano group, a nitro group, a hydroxyl group, a mercapto group, and a silyl group (for example, a trimethylsilyl group, a triisopropylsilyl group, a triphenylsilyl group, and a phenyldiethylsilyl group).

These substituents may be substituted with the above substituents. Further, these substituents may be bound together to form a ring.

At least one of $R_{01}$ is an aromatic hydrocarbon ring or an aromatic heterocyclic ring, but a phenyl group, thienyl group, pyridyl group, imidazolyl group, and pyrazolyl group are preferable. Of these, a phenyl group is more preferably utilized.

Further, $Y_{01}$ and $Y_{02}$ each represent a carbon atom or a nitrogen atom.

In Formula (1), $M_{01}$ represents a transition metal element of the 8th-10th groups of the periodic table of elements, but of these, iridium and platinum are preferably utilized.

In Formula (1), the rings A and B each represent a single five-membered ring, and the bonds to each form the rings A and B represent a single bond or a double bond.

Examples of a carbon ring of the single five-membered ring utilized as the ring A include a cyclopentane ring and a cyclopentadiene ring.

As a heterocyclic ring of the single five-membered ring utilized as the ring A, there are preferably utilized a furan ring, thiophene ring, selenophene ring, tellurophene ring, oxazole ring, isoxazole ring, oxadine ring, pyrrole ring, pyrazole ring, oxadiazole ring, triazole ring, imidazole ring, pyrazole ring, triazole ring, isothiazole ring, pyrrolidine ring, pyrazolidine ring, imidazolidine ring, isoxazolidine ring, and isothiazolidine ring.

The single five-membered ring utilized as the ring B is synonymous with the heterocyclic ring of the single five-membered ring described as the ring $Z_1$.

The single five-membered rings each formed with the rings A and B in Formula (1) incorporate $X_{01}$, $X_{02}$, $X_{03}$, $X_{04}$, $X_{05}$, and $X_{06}$, which may further have a substituent each represented by $R_{01}$ or $R_{02}$ contained in $CR_{01}$ or $NR_{02}$.

Further, the bonds to each form the rings A and B are a single bond or a double bond, but may also be a bond with a bond order such as 1.5 positioned between the single bond and the double bond.

<Metal Complex Having a Partial Structure Represented by Formula (2)>

The substituent each expressed in terms of $R_{11}$ or $R_{12}$ contained in $CR_{11}$ or $NR_{12}$ each represented by $X_{11}$, $X_{12}$, $X_{13}$, $X_{14}$, $X_{15}$, and $X_{16}$ in Formula (2) is synonymous with the substituent each expressed in terms of $R_{01}$ or $R_{02}$ contained in $CR_{01}$ or $NR_{02}$ each represented by $X_{01}$, $X_{02}$, $X_{03}$, $X_{04}$, $X_{05}$, and $X_{06}$ in Formula (1).

In Formula (2), at least one of $X_{11}$, $X_{12}$, $X_{13}$, $X_{14}$, $X_{15}$, and $X_{16}$ is $CR_{11}$.

The transition metal element of the 8th-10th groups of the periodic table of elements represented by $M_{11}$ in Formula (2) is synonymous with the transition metal element of the 8th-10th groups of the periodic table of elements each represented by Ma or $M_{01}$ in Formula (A) or (1).

The single five-membered ring represented by the ring C in Formula (2) is synonymous with the single five-membered ring represented by the ring A in Formula (1).

The single five-membered ring represented by the ring D in Formula (2) is synonymous with the single five-membered ring represented by the ring B in Formula (1).

<Metal Complex Having a Partial Structure Represented by Formula (3)>

The substituent each expressed in terms of $R_{21}$ or $R_{22}$ contained in $CR_{21}$ or $NR_{22}$ each represented by $X_{21}$, $X_{22}$, $X_{23}$, $X_{24}$, $X_{25}$, and $X_{26}$ in Formula (3) is synonymous with the substituent each expressed in terms of $R_{01}$ or $R_{02}$ contained in $CR_{01}$ or $NR_{02}$ each represented by $X_{01}$, $X_{02}$, $X_{03}$, $X_{04}$, $X_{05}$, and $X_{06}$ in Formula (1).

In Formula (3), at least one of $X_{21}$, $X_{22}$, $X_{23}$, $X_{24}$, $X_{25}$, and $X_{26}$ is $CR_{21}$.

The transition metal element of the 8th-10th groups of the periodic table of elements represented by $M_{21}$ in Formula (3) is synonymous with the transition metal element of the 8th-10th groups of the periodic table of elements each represented by Ma or $M_{01}$ in Formula (A) or (1).

The single five-membered rings represented by the rings E and F in Formula (3) are synonymous with the single five-membered ring represented by the ring B in Formula (1).

<Metal Complex Having a Partial Structure Represented by Formula (4)>

The substituent each expressed in terms of $R_{31}$ or $R_{32}$ contained in $CR_{31}$ or $-NR_{32}$ each represented by $X_{31}$, $X_{32}$, $X_{33}$, $X_{34}$, $X_{35}$, and $X_{36}$ in Formula (4) is synonymous with the substituent each expressed in terms of $R_{01}$ or $R_{02}$ contained in $CR_{01}$ or $NR_{02}$ each represented by $X_{01}$, $X_{02}$, $X_{03}$, $X_{04}$, $X_{05}$, and $X_{06}$ in Formula (1).

In Formula (4), at least one of $X_{31}$, $X_{32}$, $X_{33}$, $X_{34}$, $X_{35}$, and $X_{36}$ is $CR_{31}$.

The transition metal element of the 8th-10th groups of the periodic table of elements each represented by $M_{31}$ in Formula (4) is synonymous with the transition metal element of the 8th-10th groups of the periodic table of elements each represented by Ma or $M_{01}$ in Formula (A) or (1).

The single five-membered rings each represented by the rings G and H in Formula (4) are synonymous with the single five-membered rings each represented by the rings E and F in Formula (3).

Specific examples of the metal complex having, as a partial structure, at least one of the structures represented by Formulas (A) and (1)-(4) will now be listed, but the present invention is not limited thereto.

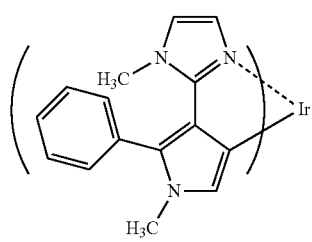

1-1

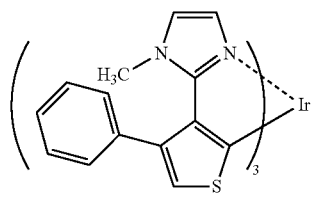

1-2

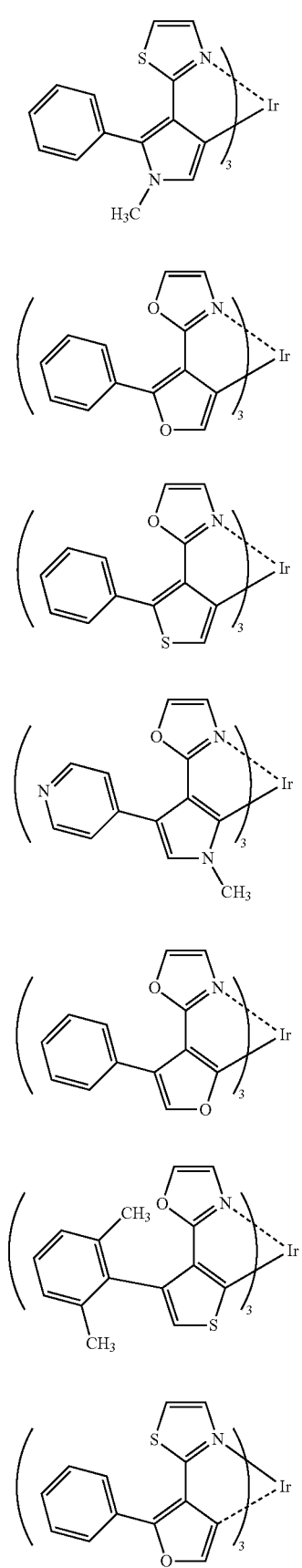
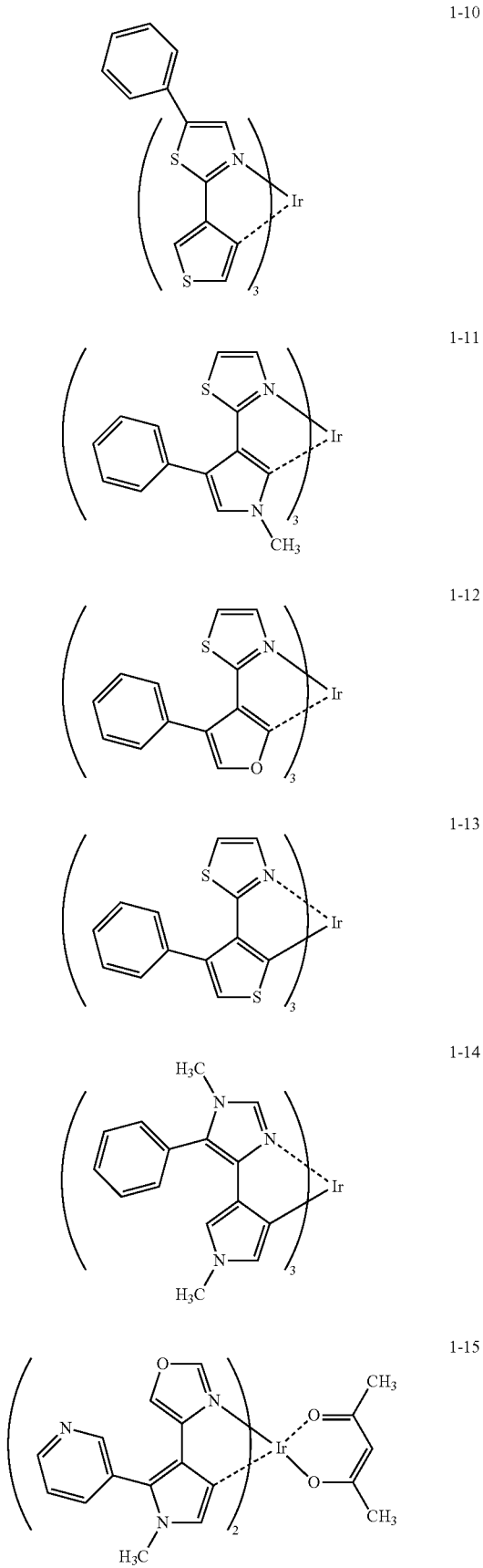

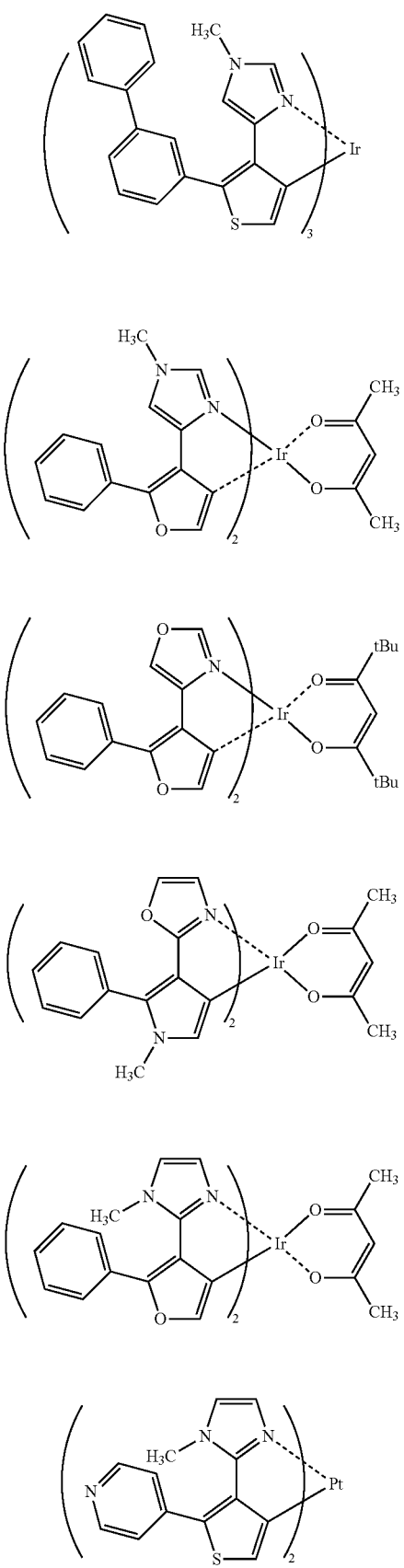
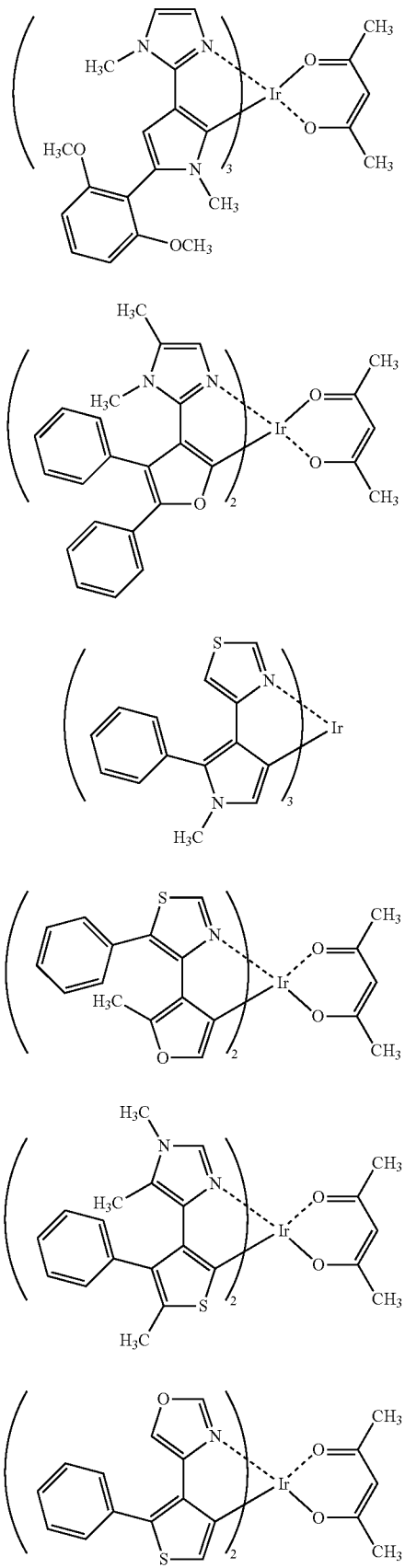

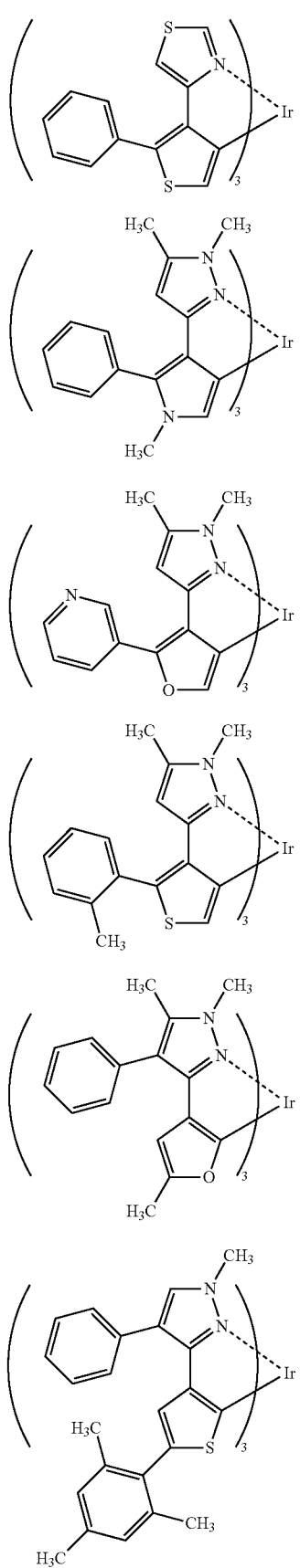
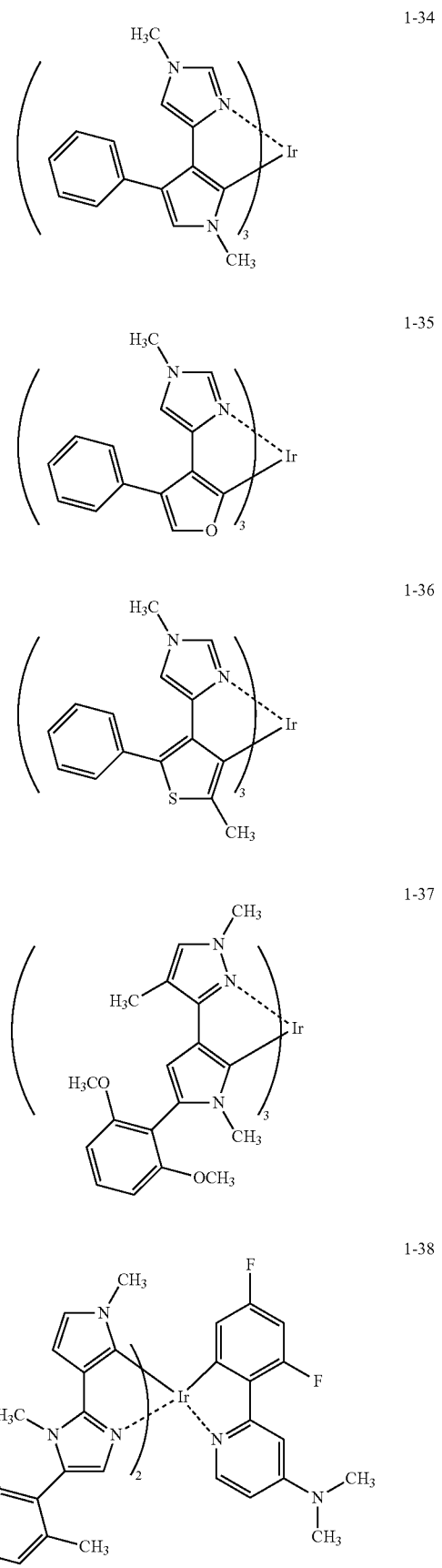

1-39
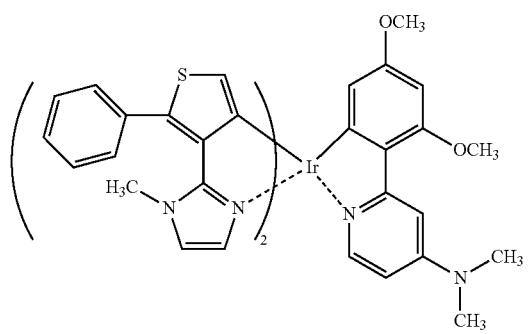
1-40
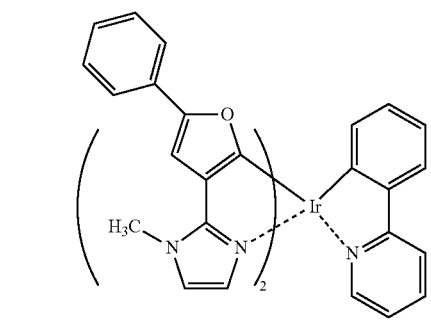
1-41
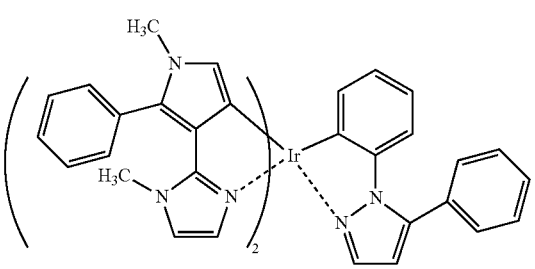
1-42
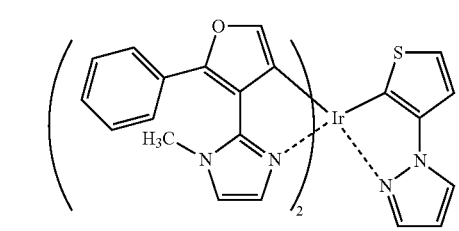
1-43
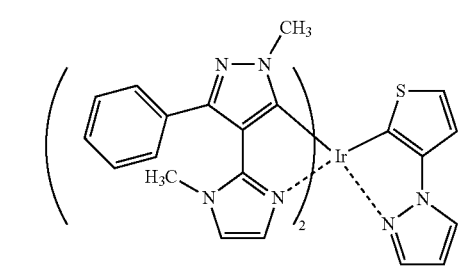
1-44
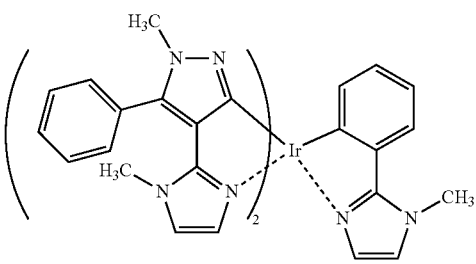
1-45
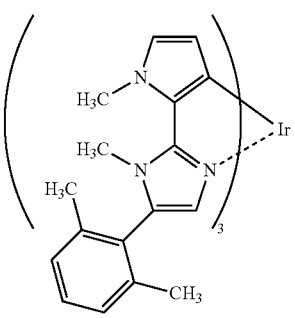
1-46
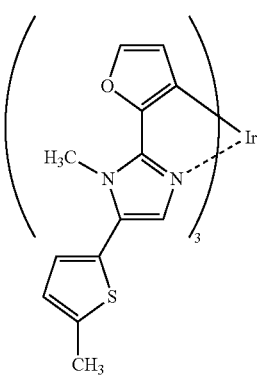
1-47
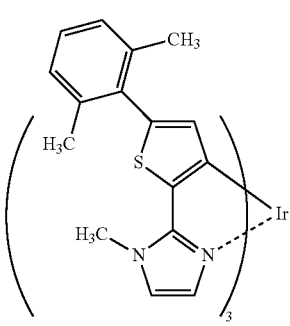
1-48
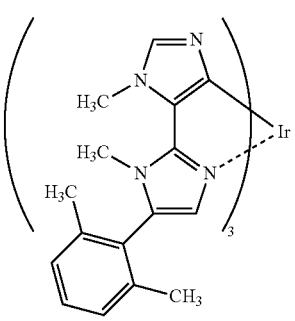

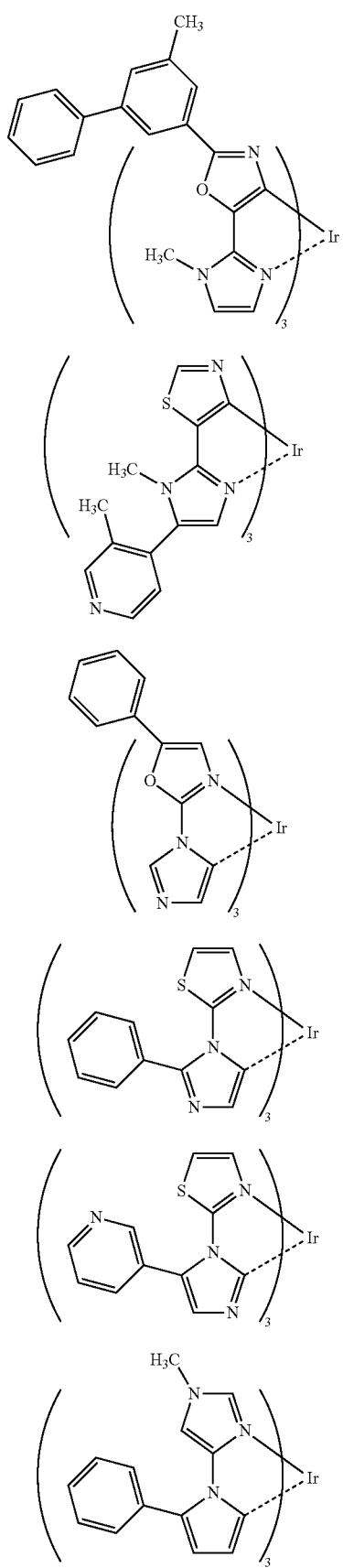
1-49
1-50
2-1
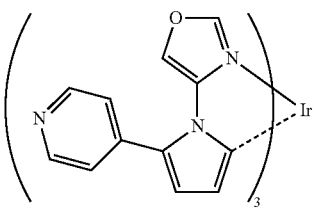
2-5
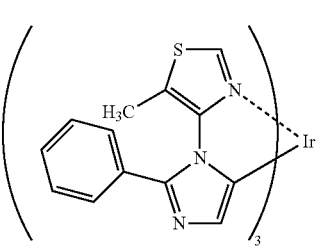
2-6
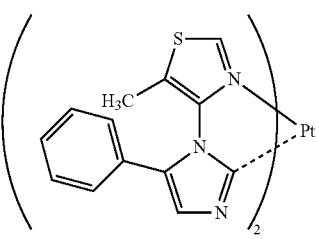
2-7
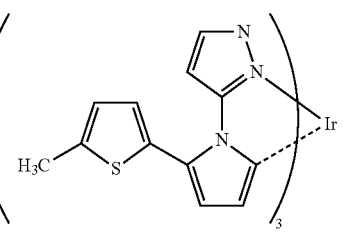
2-8
2-2
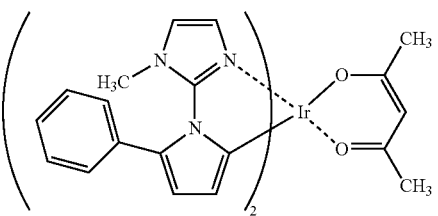
2-9
2-3
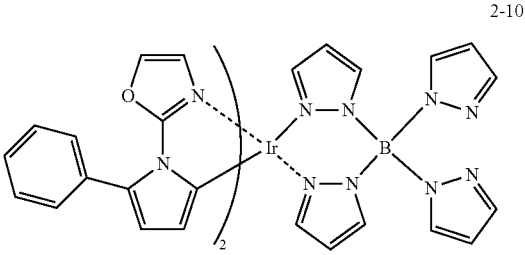
2-10
2-4
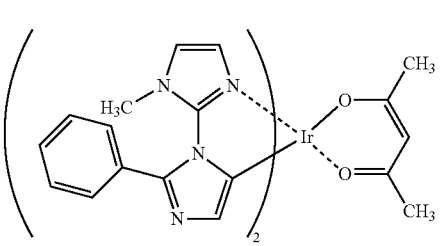
2-11

2-12
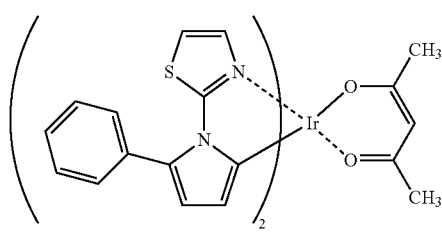
2-13
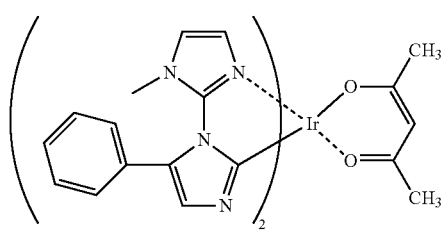
2-14
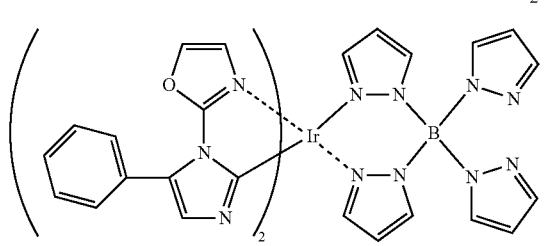
2-15
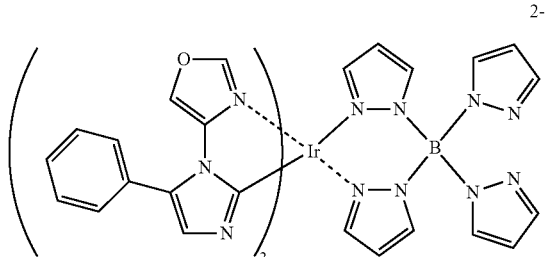
2-16
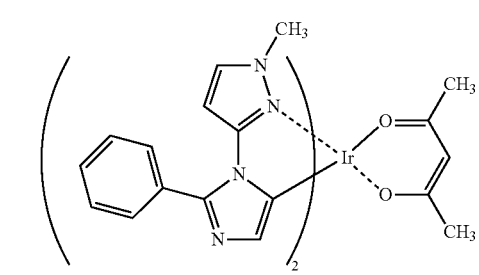
2-17
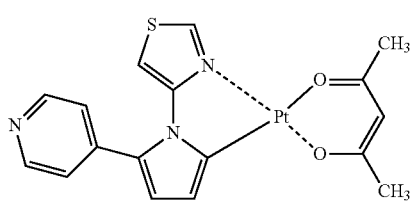
2-18
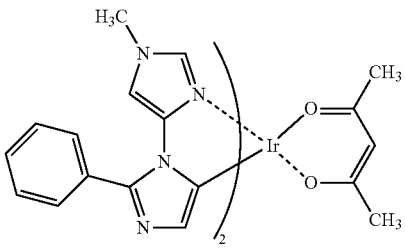
2-19
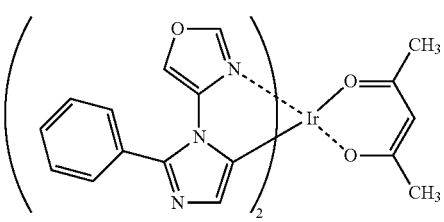
2-20
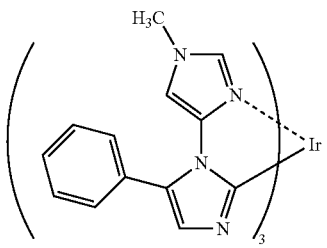
2-21
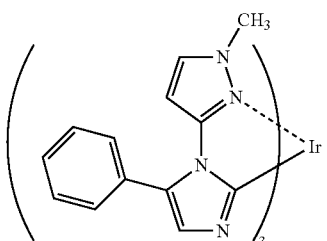
2-22
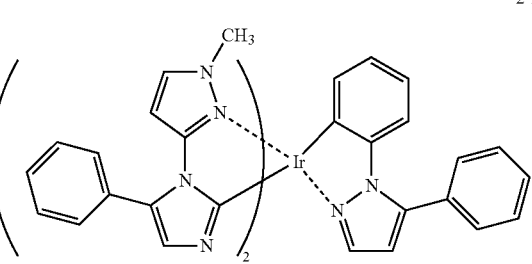
2-23
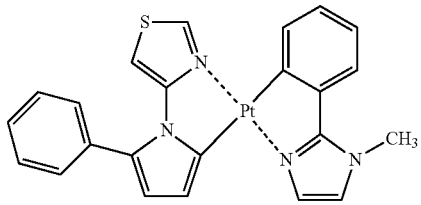

2-24 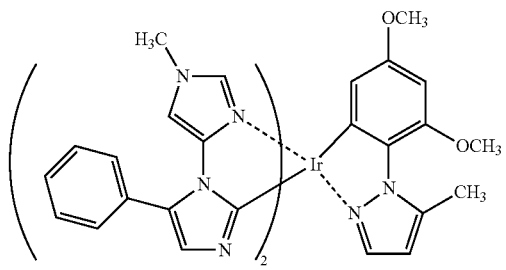
2-25 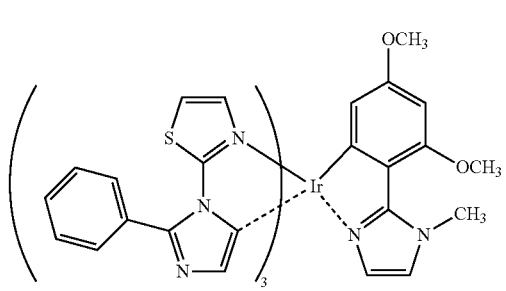
2-26 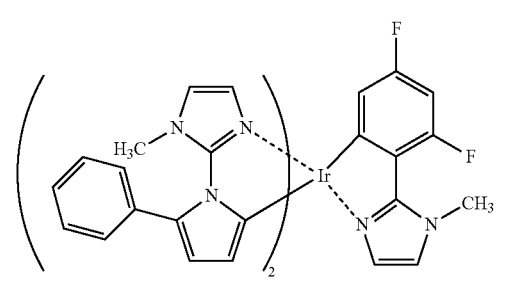
2-27 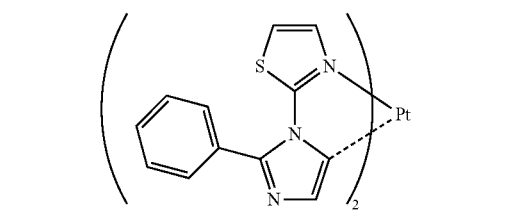
2-28 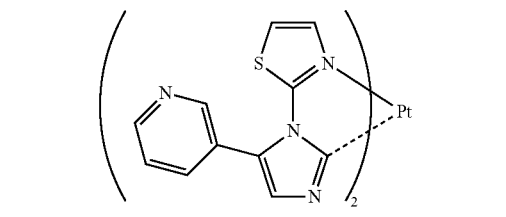
2-29 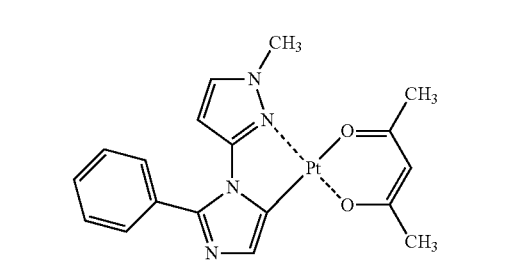
2-30 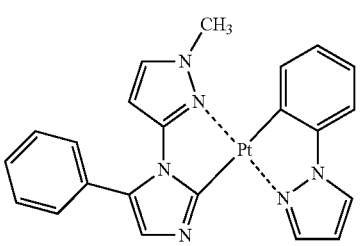
3-1 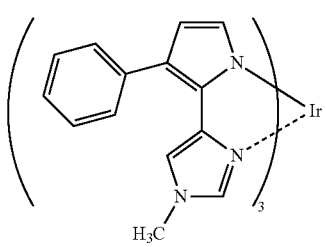
3-2 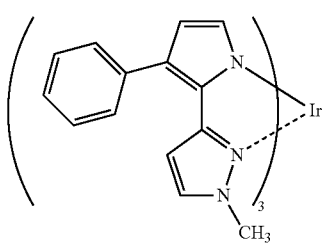
3-3 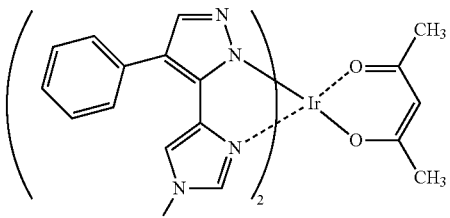
3-4 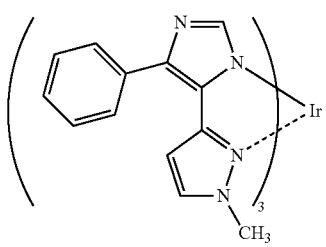
3-5

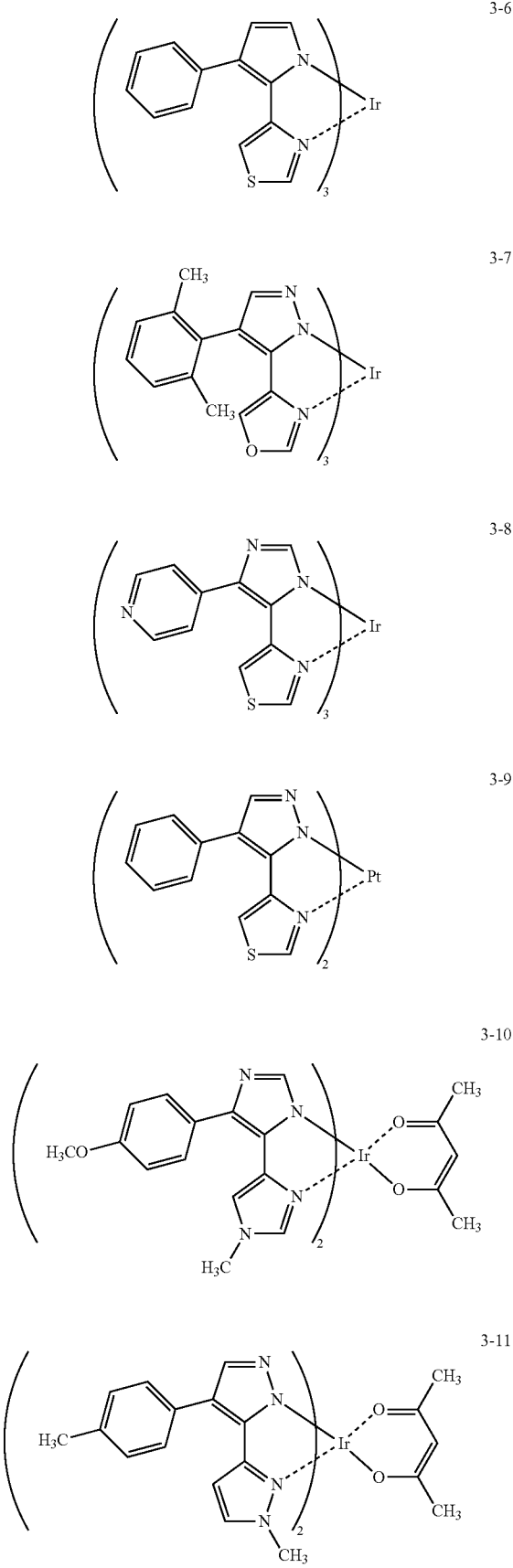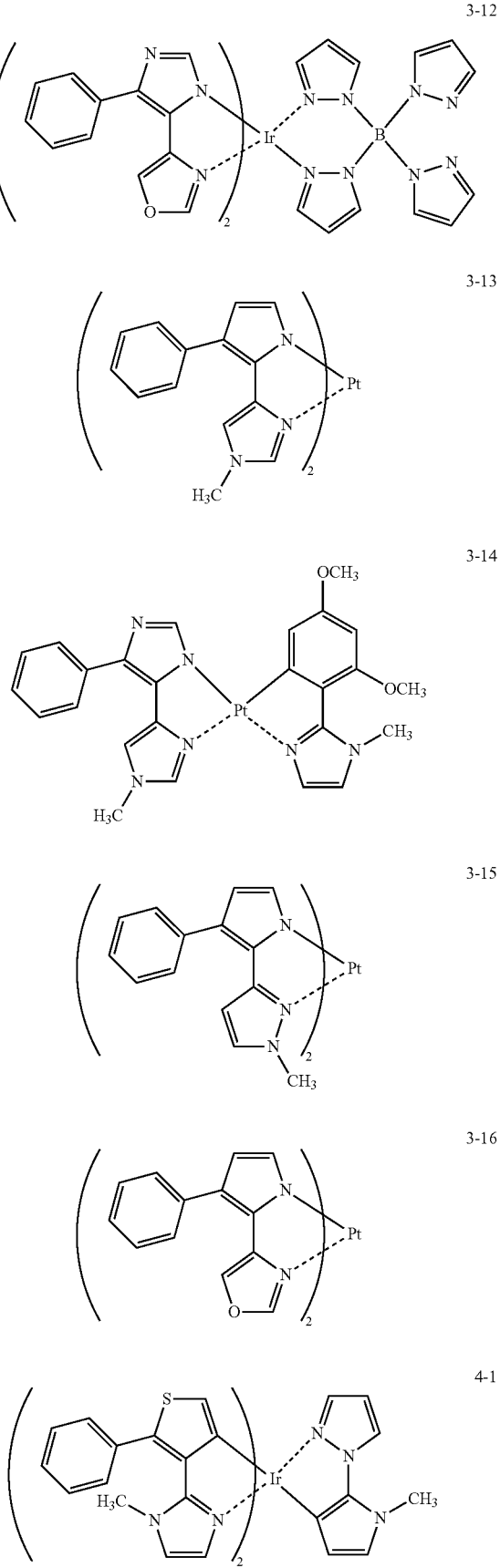

4-2
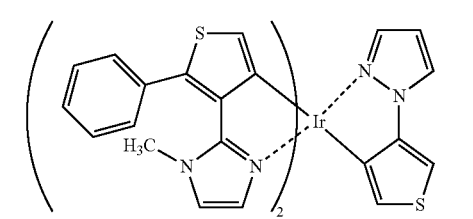
4-3
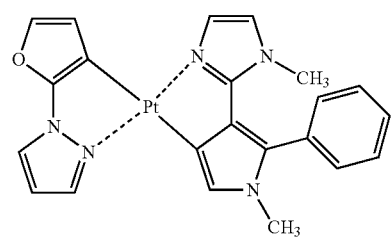
4-4
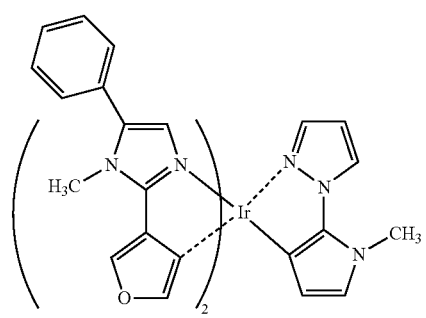
4-5
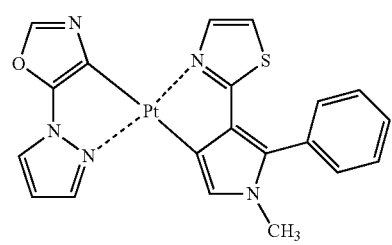
4-6
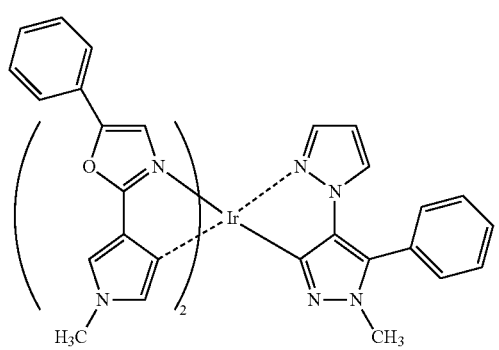
4-7
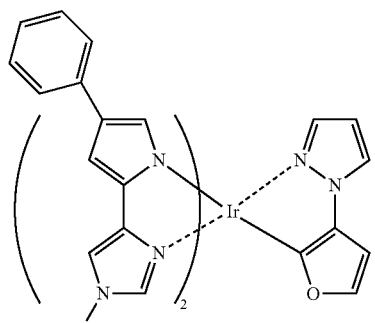
4-8
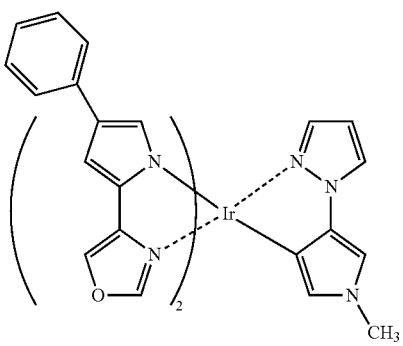
4-9
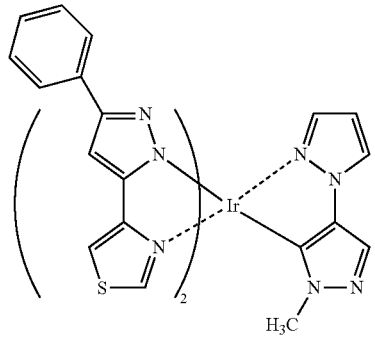
4-10
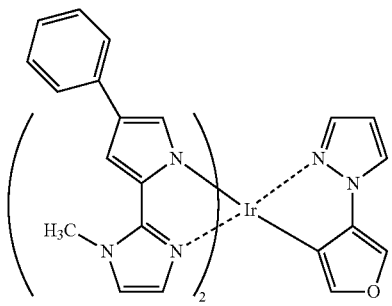
4-11
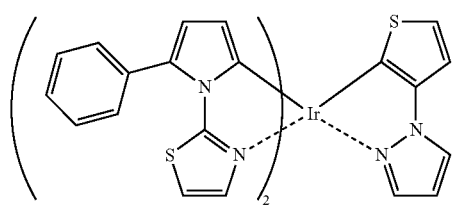

4-12

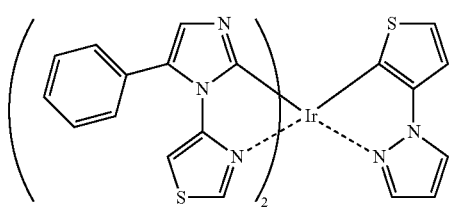

4-13

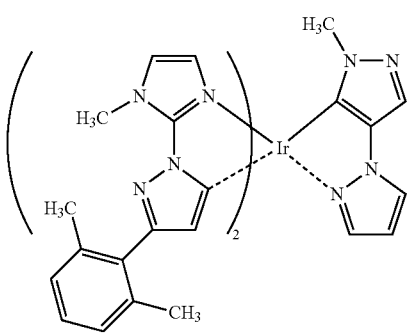

4-14

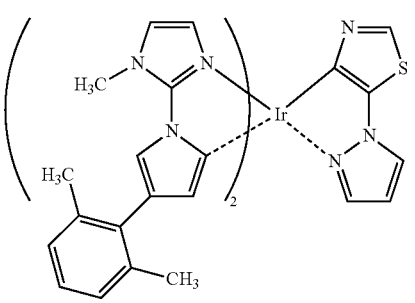

4-15

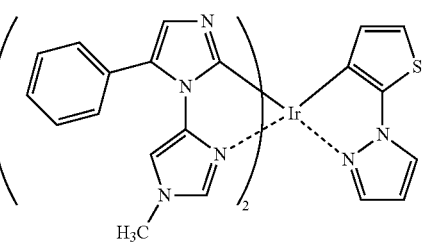

A synthetic example of Compound 4-2 will now be shown as one synthetic example of specific examples of the metal complex, but the present invention is not limited thereto.

<Synthesis of Compound 4-2>

Compound (A), compound (B), compound (C) and compound (D) used in a synthetic process of Compound 4-2 are listed below.

Compound (A)

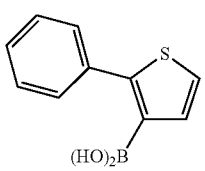

Compound (B)

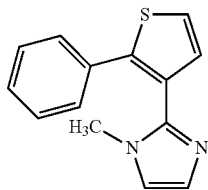

Compound (C)

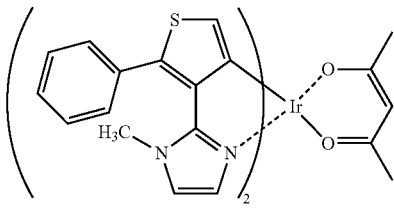

Compound (D)

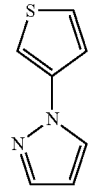

3-Bromo-2-phenylthiophene was prepared by introducing one equivalent of phenylboronic acid to 2,3-dibromothiophene via the Suzuki Coupling. The compound (A) was prepared by converting 3-bromo-2-phenylthiophene into a boronic acid via a method conventionally known in the art.

The compound (B) was prepared by allowing the compound (A) thus obtained to react with 2-bromo-1-methyl-1H-imidazole via a method conventionally known in the art employing the Suzuki Coupling.

A solution of 2-ethoxyethanol and water (a mixture ratio of 3 to 1) containing iridium chloride trihydrate and 4 equivalent, based on the same, of the compound (B) was heated to reflux at 120° C. for 6 hours, and then the resultant solid was filtered to give iridium μ complex. A solution containing the thus obtained indium μ complex was prepared by adding 3 equivalent, based on the same, of each of acetylacetone and sodium carbonate and by adding 2-ethoxyethenol, followed by being heated to reflux at 120° C. for 4 hours. The resultant organic layer was extracted with water added, followed by removal of the solvent to give the compound (C) via purification employing silica column chromatography. Tow equivalents, based on the compound (C), of the compound (D) were added to the compound (C) in glycerin, followed by being heated while stirring at 140° C. for 4 hours. The organic layer was extracted with water added, followed by removal of the solvent to give Compound 4-2 via purification employing silica column chromatography.

Metal complexes according to an organic EL element material of this invention can be synthesized by applying a method described in such as Organic Letter, vol. 3, No. 16, pp. 2579-2581 (2001), Inorganic Chemistry vol. 30, No. 8, pp. 1685-1687 (1991), J. Am. Chem. Soc., vol. 123, p. 4304 (2001), Inorganic Chemistry vol. 40, No. 7, pp. 1704-1711 (2001), Inorganic Chemistry vol. 41, No. 12, pp. 3055-3066 (2002), New Journal of Chemistry, vol. 26, p. 1171 (2002), European Journal of Organic Chemistry Vol. 4, pp. 95-709 (12004), and reference documents described in these documents.

<Application of Organic EL Element Material Containing Metal Complex to Organic EL Element>

In the case of preparing an organic EL element by utilizing an organic EL element material of this invention, said material is preferably utilized in an emission layer or an electron inhibition layer among constituent layers (details will be described later) of the organic EL element. Further, the material is preferably utilized as an emission dopant in an emission layer as described above.

(Emission Host and Emission Dopant)

A mixing ratio of an emission dopant against an emission host as a primary component in an emission layer, is preferably adjusted to a range of 0.1-30 weight %.

However, plural types of compounds may be utilized in combination as an emission dopant, and the partner to be mixed may be a metal complex having a different structure, and a phosphorescent dopant or a fluorescent dopant having other structures.

Here, a dopant (such as a phosphorescent dopant and a fluorescent dopant) which may be utilized together with a metal complex employed as an emission dopant will be described.

An emission dopant is roughly classified into two types, that is, a fluorescent dopant which emits fluorescence and a phosphorescent dopant which emits phosphorescence.

A typical example of the former (a fluorescent dopant) includes coumarin type dye, pyran type dye, cyanine type dye, croconium type dye, squarylium type dye, oxobenzanthracene type dye, fluorescein type dye, rhodamine type dye, pyrylium type dye, perylene type dye, stilbene type dye, polythiophene type dye or rare earth complex type fluorescent substances.

A typical example of the latter (a phosphorescent dopant) is preferably a complex type compound containing metal of the 8th-10th groups of the periodic table, more preferably an iridium compound and an osmium compound and most preferable among them is an iridium compound.

Specifically, listed are compounds described in the following patent publication:

Such as WO 00/70655, JP-A Nos. 2002-280178, 2001-181616, 2002-280179, 2001-181617, 2002-280180, 2001-247859, 2002-299060, 2001-313178, 2002-302671, 2001-345183 and 2002-324679, WO 02/15645, JP-A Nos. 2002-332291, 2002-50484, 2002-322292 and 2002-83684, Japanese Translation of PCT International Application Publication No. 2002-540572, JP-A Nos. 2002-117978, 2002-338588, 2002-170684 and 2002-352960, WO 01/93642 pamphlet, JP-A Nos. 2002-50483, 2002-100476, 2002-173674, 2002-359082, 2002-175884, 2002-363552, 2002-184582 and 2003-7469, Japanese Translation of PCT International Application Publication No. 2002-525808, JP-A 2003-7471, Japanese Translation of PCT International Application Publication No. 2002-525833, JP-A Nos. 2003-31366, 2002-226495, 2002-234894, 2002-235076, 2002-241751, 2001-319779, 2001-319780, 2002-62824, 2002-100474, 2002-203679, 2002-343572 and 2002-203678.

A part of examples thereof will be shown below.

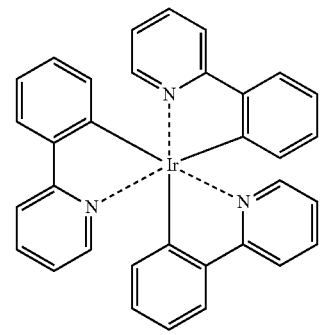

Ir-1

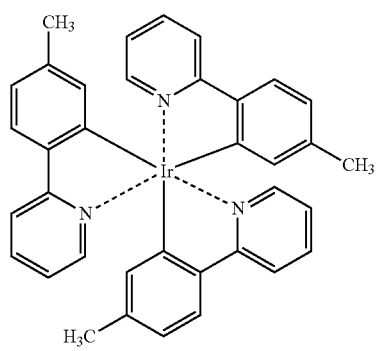

Ir-2

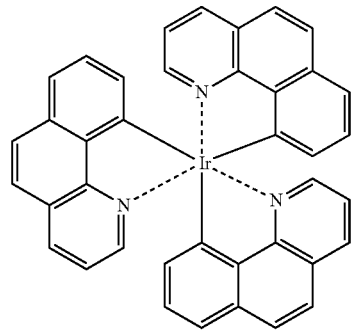

Ir-3

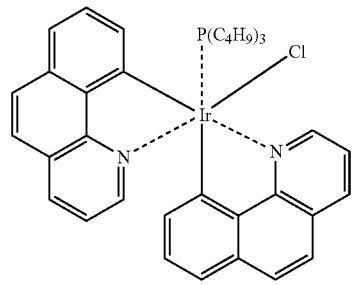

Ir-4

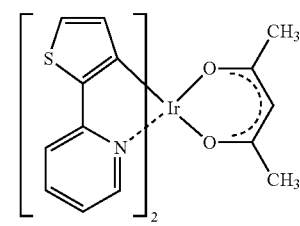

Ir-5

Ir-6
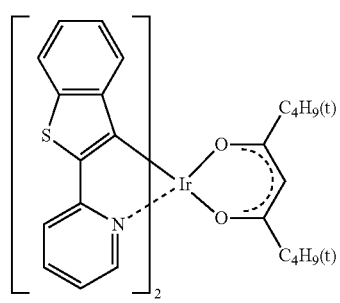
Ir-7
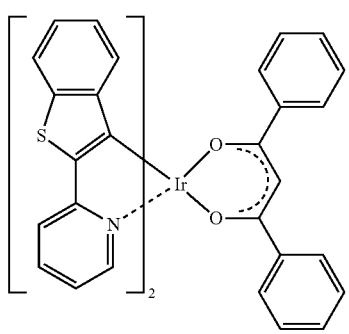
Ir-8
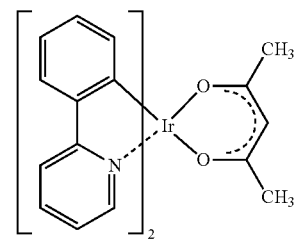
Ir-9
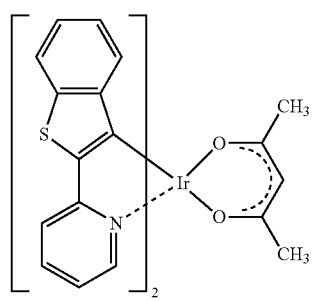
Ir-10
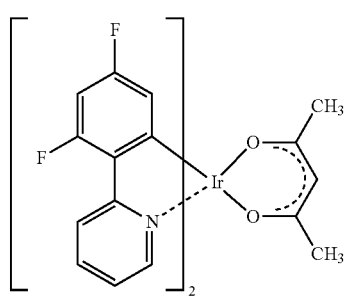
Ir-11
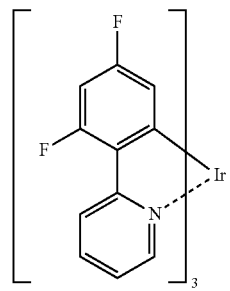
Ir-12
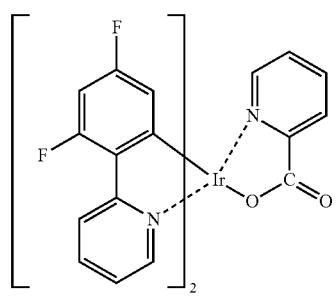
Ir-13
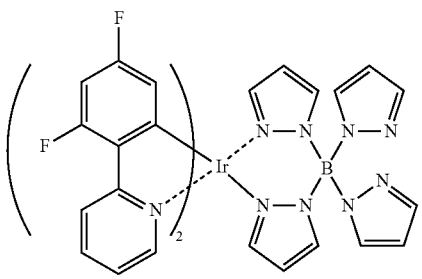
Pt-1
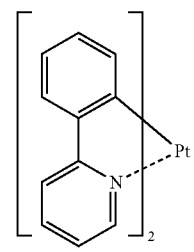
Pt-2
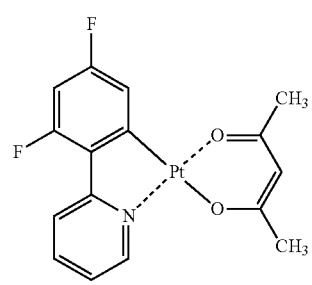

Pt-3

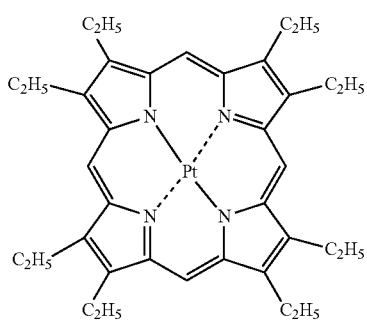

A-1

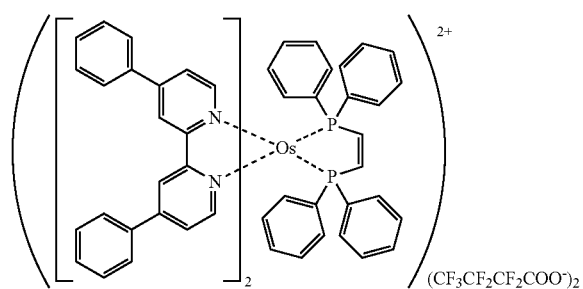

(Emission Hosts (or Called as Host Compounds))

A host compound, employed in the present invention, refers to a compound, among those incorporated in the emission layer, which results in a phosphorescent quantum yield of less than 0.01 during emitting phosphorescence.

Structures of the emission host (host compound) employed in the present invention are not particularly limited. Representative compounds include those having a basic skeleton such as carbazole derivatives, triarylamine derivatives, aromatic borane derivatives, nitrogen-containing heterocyclic compounds, thiophene derivatives, furan derivatives, or oligoarylene compounds, or derivatives having a ring structure in which at least one of the carbon atoms of the hydrocarbon ring, which constitutes carboline derivatives and the carboline ring of the above carboline derivatives, is substituted with a nitrogen atom.

Of these, preferably employed are carbazole derivatives, carboline derivatives and their derivatives which have a structure in which at least one carbon atom composing the hydrocarbon ring in the carboline ring is substituted with a nitrogen atom.

Specific examples of emission hosts will now be listed, however the present invention is not limited thereto. It is also preferable to employ these compounds as a positive hole inhibition material.

CA-1

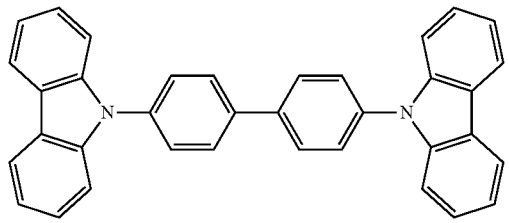

CA-2

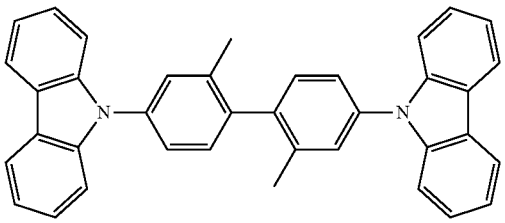

CA-3

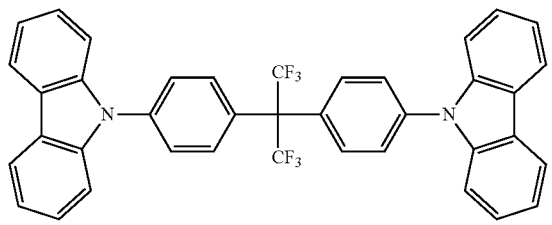

CA-4

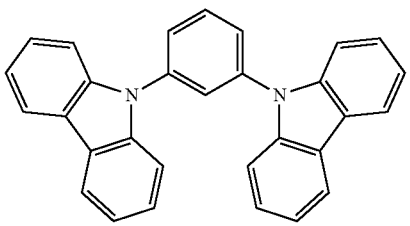

CA-5

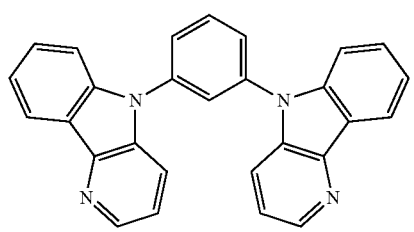

CA-6

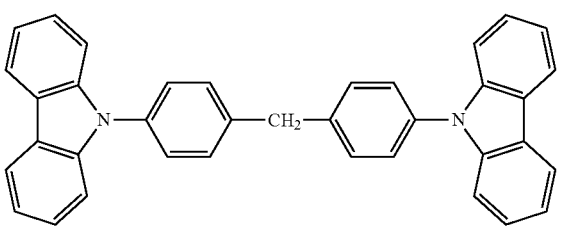

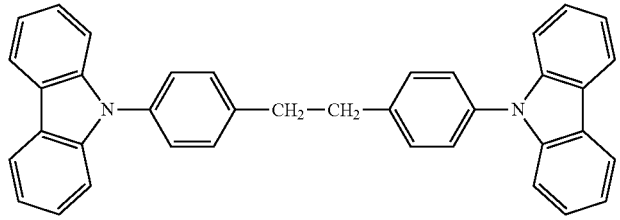
CA-7
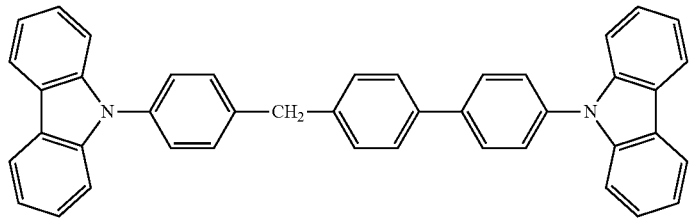
CA-8
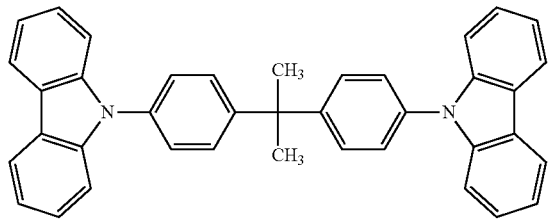
CA-9
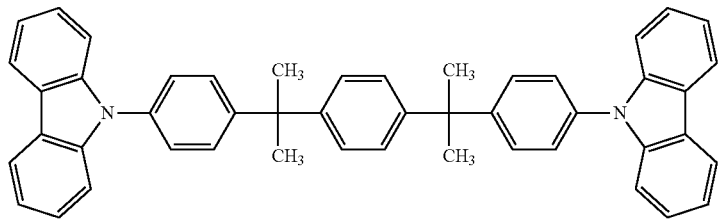
CA-10
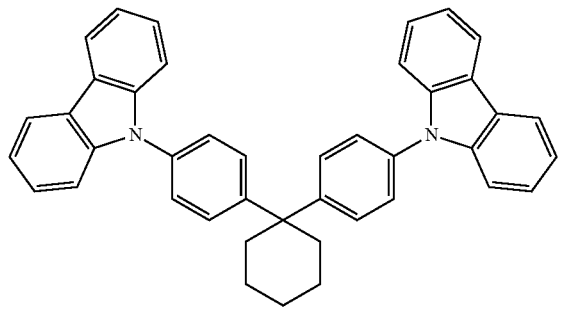
CA-11
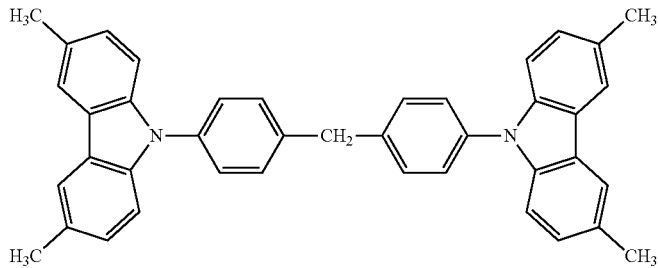
CA-12

-continued
CA-13
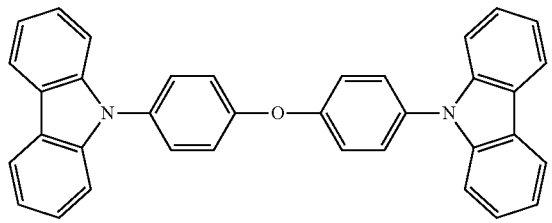
CA-14
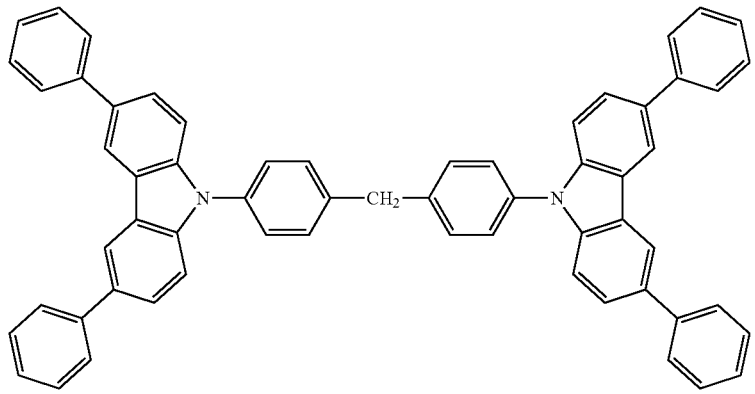
CA-15
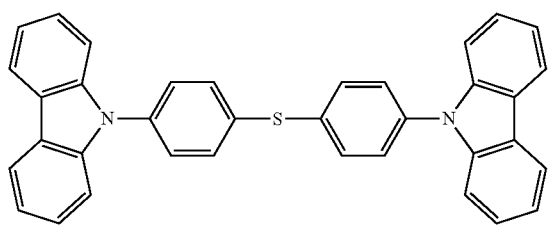
CA-16
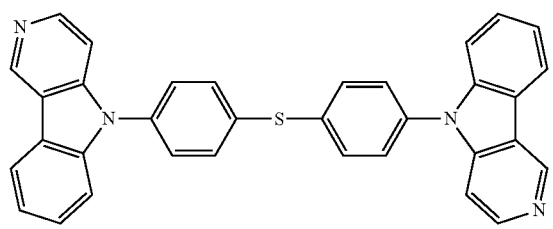
CA-17
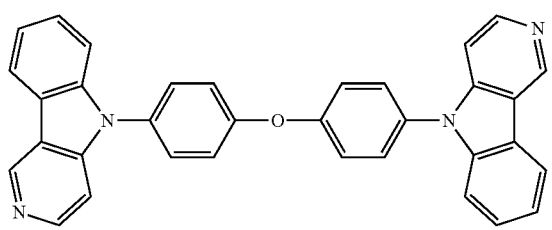
CA-18
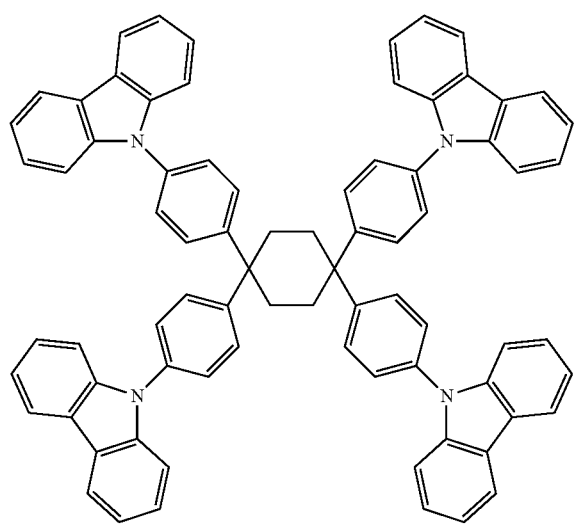
CA-19
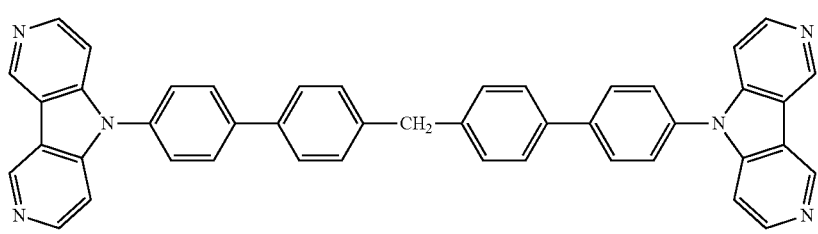

-continued

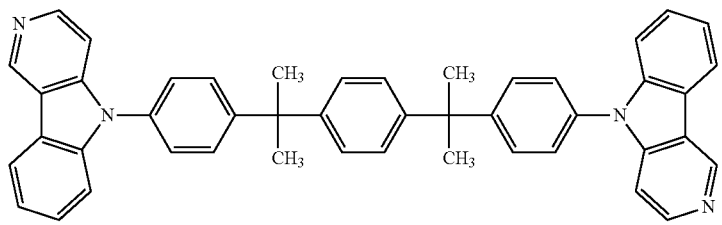
CA-20

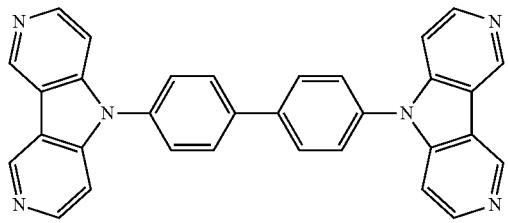
CA-21

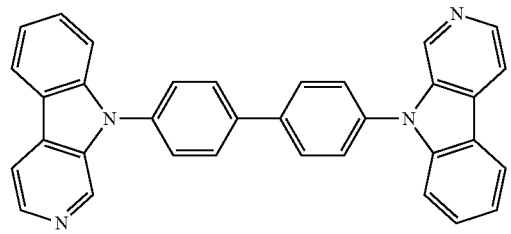
CA-22

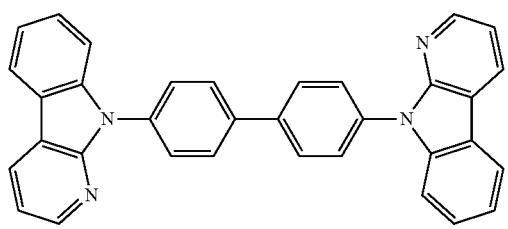
CA-23

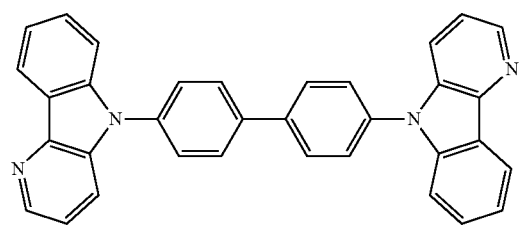
CA-24

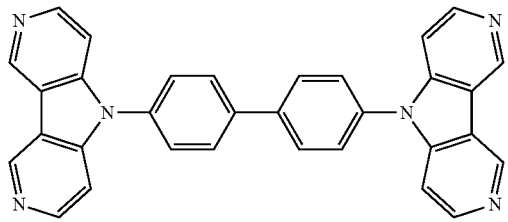
CA-25

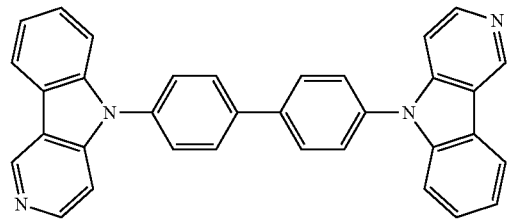
CA-26

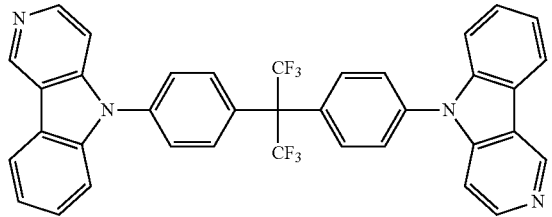
CA-27

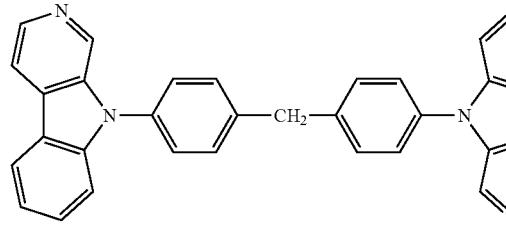
CA-28

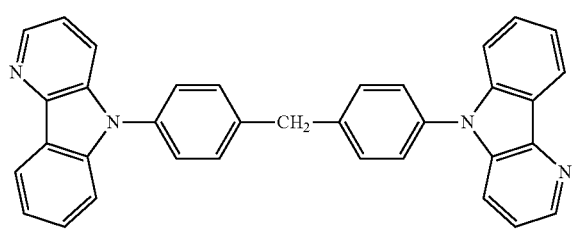
CA-29

In the emission layer according to the present invention, prior art host compounds may be employed in combinations of a plurality of types. The use of a plurality of host compounds enables regulation of migration of electrons to make organic EL elements more efficient. Preferred as these prior art host compounds are those which exhibit positive hole transportability and electron transportability, minimize the variation of luminescent wavelength to a longer wavelength, and attain a high Tg (being a glass transition temperature).

Further, an emission host of this invention may be either a low molecular weight compound or a polymer compound having a repeating unit, in addition to a low molecular weight compound provided with a polymerizing group such as a vinyl group and an epoxy group (an evaporation polymerizing emission host).

An emission host is preferably a compound having a positive hole transporting ability and an electron transporting ability, as well as preventing elongation of an emission wavelength and having a high Tg (a glass transition temperature).

As specific examples of an emission host, compounds described in the following Documents are preferable: For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837. Specific examples of an emission host are shown below; however, this invention is not limited thereto.

The emission layer may further incorporate, as a host compound, a compound which exhibits a maximum fluorescent wavelength. In such a case, luminescence is also generated from the other host compound, resulting in the maximum fluorescent wavelength in the form of electromagnetic luminescence as an organic EL element due to energy transfer from the other host compound and a phosphorescent compound to the fluorescent compound. Preferred as such host compounds resulting in the maximum fluorescent wavelength are those which attain a high fluorescent quantum yield. Herein, the fluorescent quantum yield is preferably at least 10%, but is more preferably at least 30%. Specific examples of host compounds resulting in the maximum fluorescent wavelength include coumarin based dyes, pyran based dyes, cyanine based dyes, croconium based dyes, suqualium based dyes, oxobenzanthracene based dyes, fluorescein based dyes, ROHDAMINE based dyes, pyrylium based dyes, perylene based dyes, stilbene based dyes, and polythiophene based dyes. The fluorescent quantum yield can be determined based on the method described on page 362 of Bunko (Spectroscopy) II of aforesaid Zikken Kagaku Koza (Lecture on Experimental Chemistry) 7, 4th Edition (published by Maruzen, 1992).

Next, a typical constitution of an organic EL element will be described.

<Constituent Layers of Organic EL Element>

Constituent layers of an organic EL element of this invention will now be explained.

Specific examples of a preferable layer constitution of an organic EL element of this invention are shown below; however, this invention is not limited thereto.
(i) anode/positive hole transport layer/emission layer/positive hole inhibition layer/electron transport layer/cathode,
(ii) anode/electron inhibition layer/emission layer/positive hole inhibition layer/electron transport layer/cathode,
(iii) anode/positive hole transport layer/electron inhibition layer/emission layer/positive hole inhibition layer/electron transport layer/cathode,
(iv) anode/positive hole transport layer/electron inhibition layer/emission layer/positive hole inhibition layer/electron transport layer/cathode,
(v) anode/positive hole transport layer/electron inhibition layer/emission layer/positive hole inhibition layer/electron transport layer/cathode buffer layer/cathode,
(vi) anode/anode buffer layer/positive hole transport layer/electron inhibition layer/emission layer/positive hole inhibition layer/electron transport layer/cathode buffer layer/cathode,
(vii) anode/anode buffer layer/positive hole transport layer/electron inhibition layer/emission layer/positive hole inhibition layer/electron transport layer/cathode buffer layer/cathode.

<Inhibition Layer (Electron Inhibition Layer, Positive Hole Inhibition Layer)>

An inhibition layer (such as an electron inhibition layer, a positive hole inhibition layer) according to this invention will now be explained.

In this invention, an organic EL element material of this invention is preferably utilized in such as a positive hole inhibition layer and an electron inhibition layer, and specifically preferably in a positive hole inhibition layer.

In the case of an organic EL element material of this invention being contained in a positive hole inhibition layer and an electron inhibition layer, a metal complex according to this invention, which is described in any one of the above-described embodiments 1-7, may be contained in a state of 100 weight % as a layer constituent component of such as a positive hole inhibition layer and an electron inhibition layer, or may be contained by being mixed with another organic compound (such as compounds utilized in a constituent layer of an organic EL element of this invention).

The layer thickness of an inhibition layer according to this invention is preferably 3-100 nm and more preferably 5-30 nm.

<Positive Hole Inhibition Layer>

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron.

As a positive hole inhibition layer, for example, a positive inhibition layer described in such as JP-A Nos. 11-204258 and 11-204359 and p. 273 of "Organic EL Elements and Industrialization Front Thereof (Nov. 30 (1998), published by N. T. S Corp.)" is applicable to a positive hole inhibition (hole block) layer according to this invention. Further, a constitution of an electron transport layer described later can be appropriately utilized as a positive hole inhibition layer according to this invention.

It is preferable that the organic EL layer of the present invention incorporates a positive hole layer, which incorporates derivatives having a ring structure, in which at least one carbon atom of the hydrocarbon ring constituting the above carboline derivative or the carboline ring of the above carboline derivative is substituted with a nitrogen atom.

<Electron Inhibition Layer>

On the other hand, an electron inhibition layer is, in a broad meaning, provided with a function of a positive hole transport layer, being comprised of a material having a function of transporting a positive hole but a very small ability of transporting an electron, and can improve the recombination probability of an electron and a positive hole by inhibiting an electron while transporting a positive hole. Further, a constitution of a positive hole transport layer described later can be appropriately utilized as an electron inhibition layer.

Further, in this invention, it is preferable to utilize an organic EL element material of this invention described above in an adjacent layer neighboring to an emission layer, that is in a positive hole inhibition layer and an electron inhibition layer, and specifically preferably in a positive hole inhibition layer.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is not specifically limited and can be arbitrary selected from those such as generally utilized as a charge injection transporting material of a positive hole in a conventional photoconductive material and those which are well known in the art and utilized in a positive hole injection layer and a positive hole transport layer of an EL element.

A positive hole transport material is those having any one of a property to inject or transport a positive hole or a barrier property to an electron, and may be either an organic substance or an inorganic substance. For example, listed are a triazole derivative, an oxadiazole derivative, an imidazole derivative, a polyallylalkane derivative, a pyrazolone derivative, a phenylenediamine derivative, a allylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a positive hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminophenylether; 4,4'-bis(diphenylamino)quarterphenyl; N,N,N-tri(p-tolyl)amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 5,061,569, such as 4,4'-bis[N-(1-naphthyl)-N-phenylamino] biphenyl (NDP), and 4,4',4"-tris[N-(3-methylphenyl)-N-phenylamino]triphenylamine (MDTDATA), in which three of triphenylamine units are bonded in a star burst form, described in JP-A 4-308688.

Polymer materials, in which these materials are introduced in a polymer chain or constitute the main chain of polymer, can be also utilized.

Further, an inorganic compound such as a p type-Si and a p type-SiC can be utilized as a positive hole injection material and a positive hole transport material This positive hole transport layer can be prepared by forming a thin layer made of the above-described positive hole transport material according to a method well known in the art such as a vacuum evaporation method, a spin coating method, a cast method, an inkjet method and a LB method. The layer thickness of a positive hole transport layer is not specifically limited, however, is generally 5-5,000 nm. This positive transport layer may have a single layer structure comprised of one or not less than two types of the above described materials.

<Electron Transport Layer>

An electron transfer layer is comprised of a material having a function to transfer an electron, and an electron injection layer and a positive hole inhibition layer are included in an electron transfer layer in a broad meaning. A single layer or plural layers of an electron transfer layer may be provided.

Conventionally, as an electron transfer material utilized in a single layer of an electron transfer layer, and in an electron transfer layer adjacent to the cathode side against an emission layer in the case of utilizing plural electron transfer layers, the following materials are known.

Further, an electron transfer layer is provided with a function to transmit an electron injected from a cathode to an emission layer, and compounds conventionally well known in the art can be utilized by arbitrarily selection as a material thereof.

Examples of a material utilized in this electron transfer layer (hereinafter, referred to as an electron transfer material) include such as a nitro-substituted fluorene derivative, a diphenylquinone derivative, a thiopyradineoxide derivative, a heterocyclic tetracarbonic acid anhydride such as naphthaleneperylene, carbodiimide, a fluorenylidenemethane derivative, anthraquinonedimethane and anthrone derivatives, and an oxadiazole derivative. Further, a thiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transfer material.

Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol) aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transfer material. Further, metal-free or metal phthalocyanine, or those the terminal of which is substituted by an alkyl group and a sulfonic acid group, can be preferably utilized as an electron transfer material. Further, distyrylpyrazine derivative, which has been exemplified as a material of an emission layer, can be also utilized as an electron transfer material, and, similarly to the case of a positive hole injection layer and a positive hole transfer layer, an inorganic semiconductor such as an n-type-Si and an n-type-SiC can be also utilized as an electron transfer material.

This electron transport layer can be prepared by forming a thin layer made of the above-described electron transport material according to a method well known in the art such as a vacuum evaporation method, a spin coating method, a cast method, an inkjet method and a LB method. The layer thickness of an electron transport layer is not specifically limited; however, is generally 5-5,000 nm. This electron transport layer may have a single layer structure comprised of one or not less than two types of the above described materials.

Next, an injection layer which is known as a constituent layer of an organic EL element of this invention will be explained.

<Injection Layer>: Electron Injection Layer, Positive Hole Injection Layer

An injection layer is appropriately provided and includes an electron injection layer and a positive hole injection layer, which may be arranged between an anode and an emission layer or a positive transfer layer, and between a cathode and an emission layer or an electron transfer layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a positive hole injection layer (an anode buffer layer) and an electron injection layer (a cathode buffer layer).

An anode buffer layer (a positive hole injection layer) is also detailed in such as JP-A 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polythiophene.

A cathode buffer layer (an electron injection layer) is also detailed in such as JP-A 6-325871, 9-17574 and 10-74586, and specific examples include a metal buffer layer comprising such as strontium and aluminum, an alkali metal compound buffer layer comprising such as lithium fluoride, an alkali earth metal compound buffer layer comprising such as magnesium fluoride, and an oxide buffer layer comprising such as aluminum oxide.

The above-described buffer layer (injection layer) is preferably a very thin layer, and the layer thickness is preferably in a range of 0.1-100 nm although it depends on a raw material.

This injection layer can be prepared by forming a thin layer made of the above-described material according to a method well known in the art such as a vacuum evaporation method, a spin coating method, a cast method, an inkjet method and a LB method. The layer thickness of an injection layer is not specifically limited; however, is generally 5-5,000 nm. This injection layer may have a single layer structure comprised of one or not less than two types of the above described materials.

<Anode>

As an anode according to an organic EL element of this invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), $SnO_2$ and ZnO. Further, a material such as IDIXO ($In_2O_2$—ZnO), which can prepare an amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 μm), a pattern may be formed through a mask of a desired form at the time of evaporation or spattering of the above-described substance. When emission is taken out of this anode, the transmittance is preferably set to not less than 10% and the sheet resistance as an anode is preferably not more than a few hundreds Ω/□. Further, although the layer thickness depends on a material, it is generally selected in a range of 10-1,000 nm and preferably of 10-200 nm.

<Cathode>

On the other hand, as a cathode according to this invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal. Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum. As for a cathode, these electrode substances may be made into a thin layer by a method such as evaporation or spattering. Further, the sheet resistance as a cathode is preferably not more than a few hundreds Ω/□ and the layer thickness is generally selected in a range of 10-1,000 nm and preferably of 10-200 nm. Herein, to transmit emission, either one of an anode or a cathode of an organic EL element is preferably transparent or translucent to improve the mission luminance.

<Substrate (Also Referred to as Base Plate, Base Material or Support)>

A substrate according to an organic EL element of this invention is not specifically limited with respect to types of such as glass and plastics provided being transparent, however, a substrate preferably utilized includes such as glass, quartz and transparent resin film. A specifically preferable substrate is resin film capable of providing an organic EL element with a flexible property.

Resin film includes such as film comprised of polyethylene terephthalate (PET), polyethylene naphthalate (PEN), polyether sulphone (PES), polyether imide, polyether etherketone, polyphenylene sulfide, polyallylate, polyimide, polycarbonate (PC) and cellulose acetate propionate (CAP).

On the surface of resin film, an inorganic or organic cover layer or a hybrid cover layer comprising the both may be formed, and the film is preferably provided with a high barrier ability having a vapor transmittance of not more than 0.01 $g/m^2 \cdot day$ at a temperature of 25±0.5° C., relative humidity (90±2) % RH, measured based on JIS K 7129-1992.

The taking out efficiency of emission of an organic EL element of this invention at room temperature is preferably not less than 1% and more preferably not less than 2%. Herein, taking out quantum efficiency (%)=photon number emitted out of organic EL element/electron number flown into organic EL element×100.

Further, a hue improving filter such as a color filter may be utilized in combination.

In the case of an illumination application, roughening processed film (such as anti-glare film) can be also utilized in combination to decrease emission unevenness.

In the case of an application as a multi-color display device, the display is comprised of at least two types of organic EL elements having different emission maximum wavelengths, and a preferable example to prepare an organic EL element will now be explained.

<Preparation Method of Organic EL Element>

As an example of a preparation method of an organic EL element of this invention, a preparation method of an organic EL element, comprising anode/positive hole injection layer/positive hole transport layer/emission layer/positive hole inhibition layer/electron transport layer/cathode buffer layer/cathode, will be explained.

First, on an appropriate substrate, a thin layer comprising a desired electrode substance such as an anode electrode substance is formed by means of evaporation or spattering so as to make a layer thickness of not more than 1 µm and preferably of 10-200 nm, whereby an anode is prepared. Next, on this layer, thin layers containing organic substances of such as a positive hole injection layer, a positive hole transport layer, an emission layer, a positive hole inhibition layer and an electron transport layer are formed.

A thin layer forming method of these layers containing the organic substances includes such as a spin coat method, a cast method, an inkjet method, an evaporation method and a printing method as described before, however, a vacuum evaporation method or a spin coat method is specifically preferable with respect to easy preparation of a homogeneous layer and bare generation of pinholes. Further, a different layer forming method depending on each layer may be applied. In the case of employing an evaporation method in layer formation, the evaporation condition depends on such as the type of a utilized compound, however, is generally appropriately selected in a range of 50-450° C. as a boat heating temperature, $10^{-6}$-$10^{-2}$ Pa as a vacuum degree, 0.01-50 nm/sec as a deposition rate, −50-300° C. as a substrate temperature and 1 nm-5 µm as a layer thickness.

After formation of these layers, a thin layer comprising a cathode electrode substance is formed thereon by means of such as evaporation or spattering so as to make a layer thickness in a range of 50-200 nm to provide a cathode, whereby a desired organic EL element can be prepared. This preparation of an organic EL element is preferably carried out with one time evacuation to prepare all through from a positive hole injection layer to a cathode, however, different layer forming method may be also applied by taking out the element on the way. At that time, it is preferable to take consideration such as to perform the operation under a dry inert gas environment.

<Display Device>

A display device of this invention will now be explained. The display device of this invention includes the above-described organic EL element.

A display device of this invention may be either monochromatic or multi-colored. Here explained will be a multicolor display device. In the case of a multicolor display device, a shadow mask is provided only at the time of emission layer formation, and layers can be formed all over the surface by such as an evaporation method, a cast method, a spin coat method, an inkjet method and a printing method.

When patterning is performed only with an emission layer, the method is not specifically limited; however, preferable are an evaporation method, an inkjet method and a printing method. And patterning employing a shadow mask is preferred in the case of an evaporation method.

Further, reversing the preparation order, it is also possible to prepare layers in the order of a cathode, an electron transport layer, a positive hole inhibition layer, an emission layer, a positive hole transport layer and an anode.

When a direct current voltage is applied on the multicolor display device thus prepared, emission can be observed by application of a voltage of approximately 2-40 V setting an anode to +polarity and a cathode to −polarity. Further, no current flows and no emission generate at all even when a voltage is applied with a reversed polarity. Further, in the case of alternate current voltage being applied, emission generates only in a state of an anode being + and a cathode being −. Herein, the wave shape of alternate current may be arbitrary.

A multicolor display device can be utilized as a display device, a display and various types of emission light sources. In a display device and a display, full-colored display is possible by employing three types of organic EL elements providing blue, red and green emissions.

A display device and a display include a TV, a personal computer, a mobile instrument, an AV instrument, a character broadcast display and an information display in a car. Particularly, the display device and the display may be also utilized as a display to playback still images and moving images, and may adopt either a simple matrix (a passive matrix) mode or an active matrix mode when being utilized as a display device for moving image playback.

An illumination light source includes a home use illumination, a car room illumination, a backlight of a watch or a liquid crystal, a panel advertisement, a signal, a light source of an optical memory medium, a light source for an electrophotographic copier, a light source for an optical telecommunication processor and a light source for a photo-sensor, however, is not limited thereto.

<Lighting Device>

A lighting device of this invention will now be explained. The lighting device of this invention includes the above-described organic EL element.

An organic EL element of this invention can be utilized as an organic EL element provided with a resonator structure, and a utilization purpose of such an organic EL element provided with a resonator structure includes such as a light source for an optical memory medium, a light source for an electrophotographic copier, a light source for a optical telecommunication processor and a light source for a photo-sensor, however, is not limited thereto. Further, the organic EL element may be utilized for the above-described applications by being made to perform laser emission.

Further, an organic EL element of this invention may be utilized as one type of a lamp like an illumination and an exposure light, and may be also utilized as a display device of a projector of an image projecting type and a display device (a display) of a type to directly view still images and moving images. An operating mode in the case of being utilized as a display device for playback of moving images may be either a simple matrix (a passive matrix) mode or an active matrix mode. In addition, a full-color display device can be prepared by utilizing at least two types of organic EL elements of this invention which emit different emitting colors.

In the following, one example of a display device provided with an organic EL element of this invention will be explained.

FIG. 1 is a schematic drawing to show an example of a display device constituted of an organic EL element. It is a schematic drawing of a display, which displays image information by emission of an organic EL element, such as a mobile phone.

Display 1 is constituted of such as display section A having plural number of pixels and control section B which performs image scanning of display section A based on image information.

Control section B, which is electrically connected to display section A, sends a scanning signal and an image data signal to plural number of pixels based on image information from the outside and pixels of each scanning line successively emit depending on the image data signal by a scanning signal to perform image scanning, whereby image information is displayed on display section A.

Figure 2:
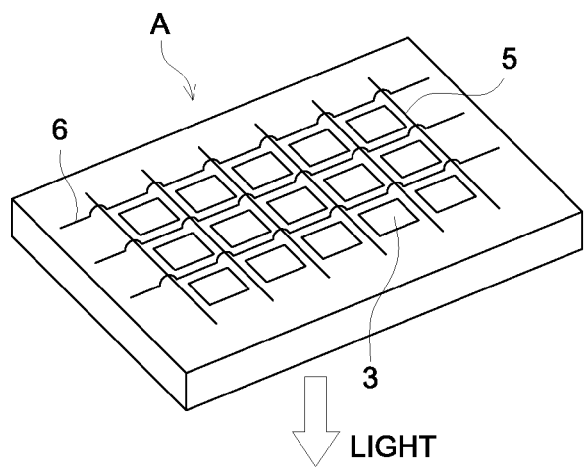
FIG. 2 is a schematic drawing of display section A.

FIG. 2 is a schematic drawing of display section A.

Display section A is provided with such as a wiring part, which contains plural scanning lines 5 and data lines 6, and plural pixels 3 on a substrate. Primary part materials of display section A will be explained in the following.

In the drawing, shown is the case that light emitted by pixel 3 is taken out along the white allow (downward).

Scanning lines 5 and plural data lines 6 in a wiring part each are comprised of a conductive material, and scanning lines 5 and data lines 6 are perpendicular in a grid form and are connected to pixels 3 at the right-angled crossing points (details are not shown in the drawing).

Pixel 3 receives an image data from data line 6 when a scanning signal is applied from scanning line 5 and emits according to the received image data. Full-color display device is possible by appropriately arranging pixels having an emission color in a red region, pixels in a green region and pixels in a blue region, side by side on the same substrate.

Next an emission process of a pixel will be explained.

Figure 3:
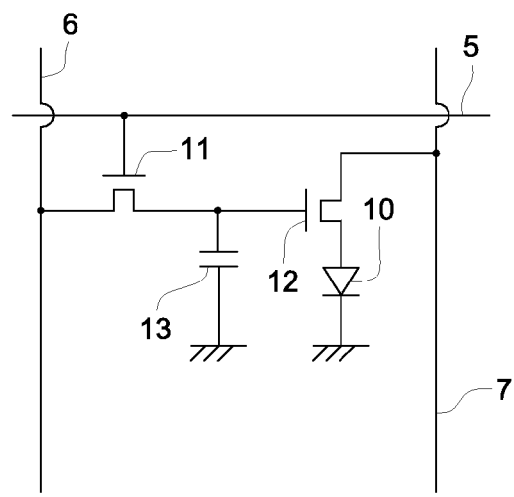
FIG. 3 is an equivalent circuit diagram of an image pixel.

FIG. 3 is a schematic drawing of a pixel.

A pixel is equipped with such as organic EL element 10, switching transistor 11, operating transistor 12 and capacitor 13. Red, green and blue emitting organic EL elements are utilized as organic EL element 10 for plural pixels, and full-color display device is possible by arranging these side by side on the same substrate.

In FIG. 3, an image data signal is applied on the drain of switching transistor 11 via data line 6 from control section B. Then, when a scanning signal is applied on the gate of switching transistor 11 via scanning line 5 from control section B, operation of switching transistor is on to transmit the image data signal applied on the drain to the gates of capacitor 13 and operating transistor 12.

Operating transistor 12 is on, simultaneously with capacitor 13 being charged depending on the potential of an image data signal, by transmission of an image data signal. In operating transistor 12, the drain is connected to electric source line 7 and the source is connected to the electrode of organic EL element 10, and an electric current is supplied from electric source line 7 to organic EL element 10 depending on the potential of an image data applied on the gate.

When a scanning signal is transferred to next scanning line 5 by successive scanning of control section B, operation of switching transistor 11 is off. However, since capacitor 13 keeps the charged potential of an image data signal even when operation of switching transistor 11 is off, operation of operating transistor 12 is kept on to continue emission of organic EL element 10 until the next scanning signal is applied. When the next scanning signal is applied by successive scanning, operating transistor 12 operates depending on the potential of an image data signal synchronized to the scanning signal and organic EL element 10 emits.

That is, emission of each organic EL element 10 of plural pixels 3 is performed by providing switching transistor 11 and operating transistor 12 against each organic EL element 10 of plural pixels 3. Such an emission method is called as an active matrix mode.

Herein, emission of organic EL element 10 may be either emission of plural gradations based on a multiple-valued image data signal having plural number of gradation potentials or on and off of a predetermined emission quantity based on a binary image data signal.

Further, potential hold of capacitor 13 may be either continuously maintained until the next scanning signal application or discharged immediately before the next scanning signal application.

In this invention, emission operation is not necessarily limited to the above-described active matrix mode but may be a passive matrix mode in which organic EL element is emitted based on a data signal only when a scanning signal is scanned.

Figure 4:
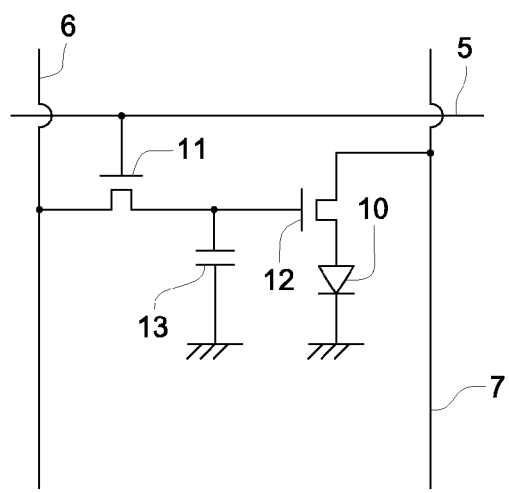
FIG. 4 is a schematic drawing of a full color display device according to a passive matrix mode.

FIG. 4 is a schematic drawing of a display device based on a passive matrix mode. In FIG. 4, plural number of scanning lines 5 and plural number of image data lines 6 are arranged grid-wise, opposing to each other and sandwiching pixels 3.

When a scanning signal of scanning line 5 is applied by successive scanning, pixel 3 connected to scanning line 5 applied with said signal emits depending on an image data signal.

Since pixel 3 is provided with no active element in a passive matrix mode, decrease of manufacturing cost is possible.

An organic EL element material of this invention can be also applied to an organic EL element to generate emission of practically white color as a lighting device. Plural emission colors are simultaneously emitted by plural number of emission materials to obtain white light by mixing colors. A combination of plural emission colors may be either the one, in which three emission maximum wavelengths of three primary colors of blue, green and red are contained, or the other, in which two emission maximum wavelengths, utilizing a relationship of complimentary colors such as blue and yellow, or blue and orange, are contained.

Further, a combination of emission materials to obtain plural number of emission colors may be either a combination comprising plural number of materials which emit phosphoresce or fluorescence, or a combination of a material which emits phosphoresce or fluorescence and a dye material which emits by light from an emission material as exiting light, however, in a white organic electroluminescent element according to this invention, it is enough only to mix plural emission dopants in combination. A mask is provided only at the time of forming such as an emission layer, a positive hole transport layer or an electron transport layer, to only simply arrange the plural emission dopants such as by separately painting through the mask, while other layers are commonly utilized to require no patterning such as a mask. Therefore, such as an electrode can be formed all over the plane by such as an evaporation method, a cast method, a spin coat method, an inkjet method and a printing method, resulting in improvement of productivity. According to this method, different from a white organic EL device in which plural colors of emission elements are arranged parallel in an alley form, an element itself is white emitting.

An emission material utilized in an emission layer is not specifically limited, and in the case of a backlight of a liquid crystal display element, any combination by arbitrary selection among platinum complexes according to this invention or emission materials well known in the art can be utilized so as to be fitted to the wavelength range corresponding to CF (color filter) characteristics, whereby white emission can be obtained.

In this manner, a white emitting organic EL element of this invention is usefully utilized as one type of a lamp such as a home use illumination, a car room illumination or an exposure light source as various emission light sources or lighting devices, in addition to the aforesaid display device and a display, and is further usefully applied for a display as such as a backlight of a liquid crystal display.

In addition to these, listed is a wide range of applications such as a backlight of a watch, an advertising board, a signal, a light source of an optical memory medium, a light source of an electrophotographic copier, a light source of an optical telecommunication processor and a light source of an optical sensor, and further general home use electric instruments which require a display device.

EXAMPLES

In the following, this invention will be explained with reference to examples, however, is not limited thereto. The compounds employed in the examples are shown below.

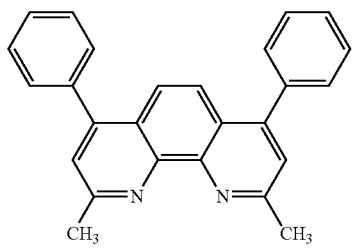

BCP

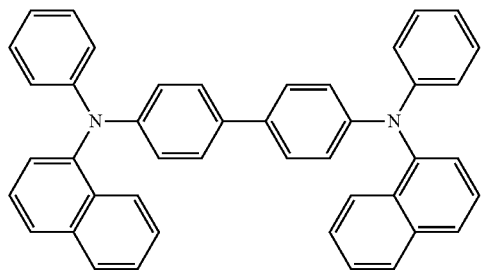

α-NPD

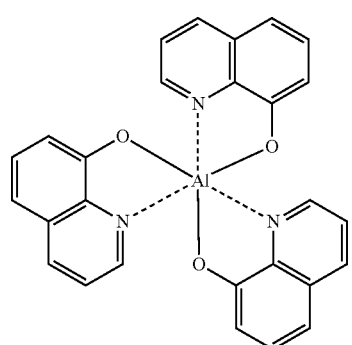

Alq3

-continued

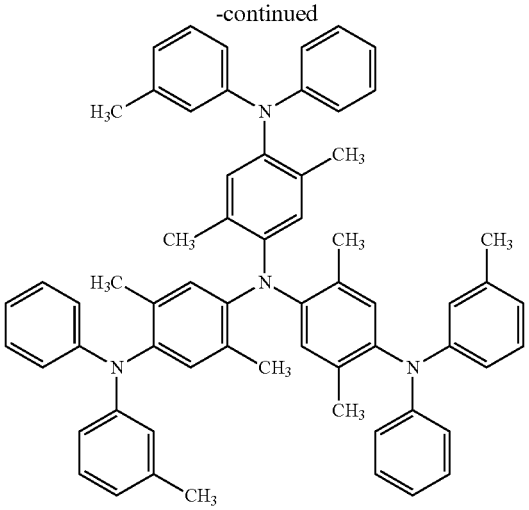

m-MTDATXA

Comparison 1

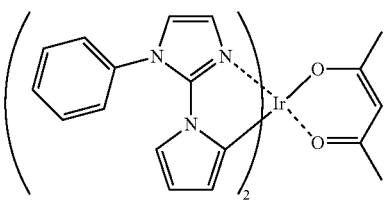

Comparison 2

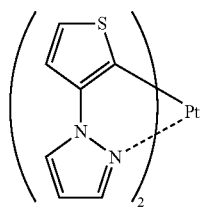

Comparison 3

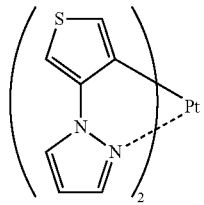

Comparison 4

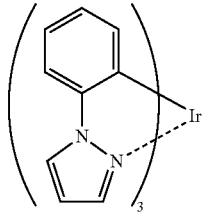

Example 1

<Preparation of Organic EL Element 1-1>

After a substrate, in which ITO had been deposited at 150 nm on a glass plate as an anode (NA-45 produced by NH Techno Glass Co. Ltd.) was subjected to patterning, the transparent support substrate was washed with isopropyl alcohol by use of ultrasonic waves, followed by being dried with a dry nitrogen gas, and was subjected to UV ozone washing for 5 minutes. This transparent support substrate was fixed on a substrate holder of a vacuum evaporation system available on the market, and on the other hand, each of five resistance heating boats made of tantalum was charged with α-NPD, CA-1, Ir-12, BCP and Alq$_3$, respectively, which was attached in the vacuum evaporation system (in the first vacuum chamber).

Further, a resistance heating boat made of tantalum was charged with lithium fluoride and a resistance heating boat made of tungsten was charged with aluminum, respectively, and these boats were attached in the second chamber of the vacuum evaporation system.

First, after the first vacuum chamber was evacuated down to $4\times10^{-4}$ Pa, the aforesaid heating boat charged with α-NPD was heated with an electric current to deposit α-NPD on a support substrate at a deposition rate of 0.1-0.2 nm/sec so as to make a layer thickness of 30 nm, whereby a positive hole injection/transport layer was formed.

Further, the aforesaid heating boat charged with CA-1 and the boat charged with Ir-12 were independently supplied with an electric current to deposit CA-1 as an emission host and Ir-12 as an emission dopant so as to make a layer thickness of 30 nm while adjusting the deposition rates thereof to 100:6, whereby an emission layer was formed.

Next, the aforesaid heating boat charged with BCP was heated with an electric current to provide a positive hole inhibition layer having a layer thickness of 10 nm at a deposition rate of 0.1-0.2 nm/sec. Further, the aforesaid heating boat charged with Alq$_3$ was heated with an electric current to provide an electron transport layer having a layer thickness of 40 nm at a deposition rate of 0.1-0.2 nm/sec.

Next, after an element having been deposited with up to an electron injection layer as described before was transferred into the second vacuum chamber while keeping vacuum, a mask, which was made of stainless steel and had rectangular holes, was arranged on the electron injection layer by means of remote control from outside of the system.

After the second vacuum chamber was evacuated down to $2\times10^{-4}$ Pa, a boat charged with lithium fluoride was supplied with an electric current to provide a cathode buffer layer having a layer thickness of 0.5 nm at a deposition rate of 0.01-0.02 nm/sec, and then a boat charged with aluminum was supplied with an electric current to provide a cathode having a layer thickness of 150 nm at a deposition rate of 1-2 nm/sec to obtain Organic EL Element 1-1.

<Preparation of Organic EL Elements 1-2 to 1-16>

Organic EL elements 1-2 to 1-16 each were prepared in a similar manner to preparation of organic EL element 1-1 described above, except that an emission host and an emission dopant was changed as shown in Table 1.

<<Evaluation of Organic EL Elements>>

When resulting Organic EL Elements 1-1 to 1-16 were evaluated, after their preparation, the non-luminescent side was covered with a glass case, and a 300 μm thick glass substrate was employed as a sealing substrate. Further, an epoxy based radiation curable type adhesive (LAXTRACK C0629B, produced by TOAGOSEI Co., Ltd.) was applied to the periphery as a sealing agent. The resulting substrate was overlapped onto the above anode to come into close contact with the above transparent supporting substrate. Subsequently, UV radiation was exposed to the glass substrate side to result in curing and sealing. Thus, the lighting device as shown in FIGS. 5 and 6 was formed and evaluation was then carried out.

Figure 5:
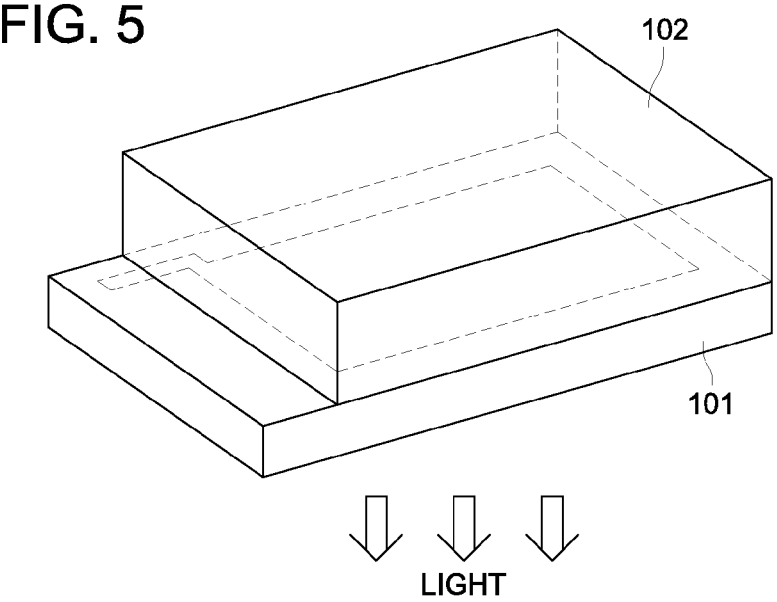
FIG. 5 is a schematic drawing of a lighting device.
Figure 6:
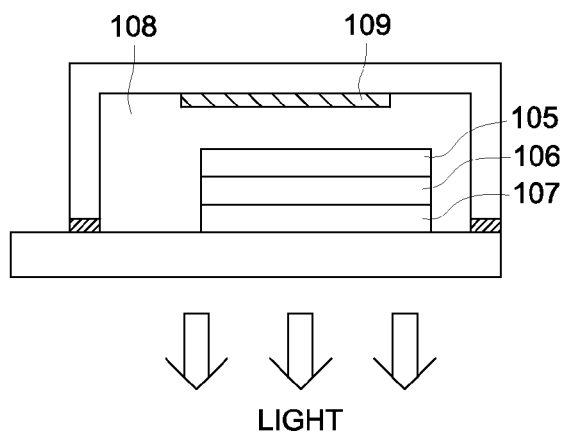
FIG. 6 is a schematic cross-sectional view of a lighting device.

FIG. 5 is a schematic view of a lighting device. Organic EL element 101 is covered with glass cover 102 (sealing operation employing the glass cover was carried out in a globe box (under an atmosphere of high purity nitrogen gas at a purity of at least 99.999%) without contact with atmospheric air). FIG. 6 is a sectional view of the lighting device, in which numeral 105 represents a cathode, 106 represents an organic EL layer, and 107 represents a glass substrate having a transparent electrode. Further, nitrogen gas 108 is fed into glass cover 102, and desiccant 109 is provided.

<Quantum Efficiency of Taking Out>

Each of organic EL elements was lighted under a constant current condition of 2.5 mA/cm$^2$ at room temperature (approximately 23-25° C.), and an emission luminance (L) [cd/m$^2$] immediately after turning on was measured, whereby a quantum efficiency of taking out (η) was calculated. Herein, CS-1000 (produced by Konica Minolta Sensing Inc.) was utilized for measurement of emission luminance. Further, each of the quantum efficiency of taking out was expressed as a relative value when that of organic EL element 1-1 was set to 100.

<Emission Life>

Each of organic EL elements was continuously lighted under a constant current condition of 2.5 mA/cm$^2$ at room temperature (approximately 23-25° C.), and time to reach a half of the initial luminance ($\tau_{1/2}$) was measured. Further, each emission life was expressed as a relative value when that of organic EL element 1-1 was set to 100.

The obtained results are shown in Table 1.

TABLE 1

| Organic EL Element No. | Emission host | Emission dopant | Taking-out Quantum Yield | Luminescent Lifetime ($\tau_{1/2}$) | Remarks |
|---|---|---|---|---|---|
| 1-1 | CA-1 | Ir-12 | 100 | 100 | Comp. |
| 1-2 | CA-1 | Comparison 1 | 91 | 109 | Comp. |
| 1-3 | CA-1 | Comparison 2 | 90 | 88 | Comp. |
| 1-4 | CA-1 | Comparison 3 | 105 | 79 | Comp. |
| 1-5 | CA-1 | 1-1 | 130 | 255 | Inv. |
| 1-6 | CA-1 | 1-2 | 134 | 314 | Inv. |
| 1-7 | CA-1 | 1-8 | 131 | 240 | Inv. |
| 1-8 | CA-1 | 1-21 | 127 | 270 | Inv. |
| 1-9 | CA-1 | 1-25 | 125 | 261 | Inv. |
| 1-10 | CA-1 | 1-28 | 132 | 312 | Inv. |
| 1-11 | CA-1 | 1-39 | 130 | 230 | Inv. |
| 1-12 | CA-1 | 1-44 | 129 | 232 | Inv. |
| 1-13 | CA-1 | 4-2 | 122 | 213 | Inv. |
| 1-14 | CA-1 | 4-5 | 120 | 204 | Inv. |
| 1-15 | CA-23 | 1-1 | 135 | 330 | Inv. |
| 1-16 | CA-23 | 1-44 | 132 | 298 | Inv. |

Based on Table 1, it is clear that the organic EL elements prepared via the metal complexes according to the present invention attain high luminescent efficiency and extended luminescent lifetime, compared to the EL element of the Comparative Examples.

Further, it was noticed that by simultaneously employing, in the emission layer, a carboline derivative or its derivative having a ring structure in which at least one carbon atom of the hydrocarbon ring constituting the carboline derivative was substituted with a nitrogen atom, targeted effects of the present invention were further enhanced.

Example 2

<Preparation of Organic EL Element 2-1>

After a substrate, in which ITO had been deposited at 150 nm on a glass plate as an anode (NA-45 produced by NH Techno Glass Co. Ltd.) was subjected to patterning, the transparent support substrate was washed with isopropyl alcohol by use of ultrasonic waves, followed by being dried with a dry nitrogen gas, and was subjected to UV ozone washing for 5 minutes.

This transparent support substrate was fixed on a substrate holder of a vacuum evaporation system available on the market, and on the other hand, each of five resistance heating boats made of tantalum was charged with α-NPD, CA-1, Ir-13, BCP and Alq$_3$, respectively, which was attached in the vacuum evaporation system (in the first vacuum chamber).

Further, a resistance heating boat made of tantalum was charged with lithium fluoride and a resistance heating boat made of tungsten was charged with aluminum, respectively, and these boats were attached in the second chamber of the vacuum evaporation system.

First, after the first vacuum chamber was evacuated down to $4 \times 10^{-4}$ Pa, the aforesaid heating boat charged with α-NPD was heated with an electric current to deposit α-NPD on a support substrate at a deposition rate of 0.1-0.2 nm/sec so as to make a layer thickness of 30 nm, whereby a positive hole injection/transport layer was formed.

Further, the aforesaid heating boat charged with CA-1 and the boat charged with Ir-13 were independently supplied with an electric current to deposit CA-1 as an emission host and Ir-13 as an emission dopant so as to make a layer thickness of 30 nm while adjusting the deposition rates thereof to 100:6, whereby an emission layer was formed.

Next, the aforesaid heating boat charged with BCP was heated with an electric current to provide a positive hole inhibition layer having a layer thickness of 10 nm at a deposition rate of 0.1-0.2 nm/sec. Further, the aforesaid heating boat charged with Alq$_3$ was heated with an electric current to provide an electron transport layer having a layer thickness of 40 nm at a deposition rate of 0.1-0.2 nm/sec.

Next, after an element having been deposited with up to an electron injection layer as described before was transferred into the second vacuum chamber while keeping vacuum, a mask, which was made of stainless steel and had rectangular holes, was arranged on the electron injection layer by means of remote control from outside of the system.

After the second vacuum chamber was evacuated down to $2 \times 10^{-4}$ Pa, a boat charged with lithium fluoride was supplied with an electric current to provide a cathode buffer layer having a layer thickness of 0.5 nm at a deposition rate of 0.01-0.02 nm/sec, and then a boat charged with aluminum was supplied with an electric current to provide a cathode having a layer thickness of 150 nm at a deposition rate of 1-2 nm/sec to obtain Organic EL Element 2-1.

<Preparation of Organic EL Elements 2-2 to 2-15>

Organic EL elements 2-2 to 2-15 each were prepared in a similar manner to preparation of organic EL element 2-1 described above, except that an emission dopant was changed as shown in Table 2.

<<Evaluation of Organic EL Elements>>

When resulting Organic EL Elements 2-1 to 2-15 were evaluated, after their preparation, the non-luminescent side was covered with a glass case, and a 300 μm thick glass substrate was employed as a sealing substrate. Further, an epoxy based radiation curable type adhesive (LAXTRACK C0629B, produced by TOAGOSEI Co., Ltd.) was applied to the periphery as a sealing agent. The resulting substrate was overlapped onto the above anode to come into close contact with the above transparent supporting substrate. Subsequently, UV radiation was exposed to the glass substrate side to result in curing and sealing. Thus, the lighting device as shown in FIGS. 5 and 6 was formed and evaluation was then carried out.

FIG. 5 is a schematic view of a lighting device. Organic EL element 101 is covered with glass cover 102 (sealing operation employing the glass cover was carried out in a globe box (under an atmosphere of high purity nitrogen gas at a purity of at least 99.999%) without contact with atmospheric air). FIG. 6 is a sectional view of the lighting device, in which numeral 105 represents a cathode, 106 represents an organic EL layer, and 107 represents a glass substrate having a transparent electrode. Further, nitrogen gas 108 is fed into glass cover 102, and desiccant 109 is provided.

Taking-out quantum efficiency was evaluated in the same manner as for Example 1. The taking-out quantum efficiency was expressed by relative values when each value of Organic EL Element 2-1 was 100.

<Emission Life>

Each of organic EL elements was continuously lighted under a constant current condition of 2.5 mA/cm$^2$ at room temperature (approximately 23-25° C.), and time to reach 90% of the initial luminance ($\tau_{1/9}$) was measured. Further, each emission life was expressed as a relative value when that of organic EL element 2-1 was set to 100.

Table 2 shows the results.

TABLE 2

| Organic EL Element No. | Emission host | Emission dopant | Taking-out Quantum Yield | Luminescent Lifetime ($\tau_{1/9}$) | Remarks |
|---|---|---|---|---|---|
| 2-1 | CA-1 | Ir-13 | 100 | 100 | Comp. |
| 2-2 | CA-1 | Comparison 1 | 83 | 103 | Comp. |
| 2-3 | CA-1 | Comparison 2 | 90 | 98 | Comp. |
| 2-4 | CA-1 | Comparison 3 | 100 | 77 | Comp. |
| 2-5 | CA-1 | 2-2 | 130 | 241 | Inv. |
| 2-6 | CA-1 | 2-7 | 128 | 255 | Inv. |
| 2-7 | CA-1 | 2-9 | 124 | 279 | Inv. |
| 2-8 | CA-1 | 2-13 | 129 | 288 | Inv. |
| 2-9 | CA-1 | 2-14 | 129 | 203 | Inv. |
| 2-10 | CA-1 | 2-17 | 122 | 277 | Inv. |
| 2-11 | CA-1 | 2-20 | 135 | 298 | Inv. |
| 2-12 | CA-1 | 2-23 | 124 | 282 | Inv. |
| 2-13 | CA-1 | 4-12 | 120 | 230 | Inv. |
| 2-14 | CA-23 | 2-2 | 133 | 345 | Inv. |
| 2-15 | CA-23 | 2-7 | 134 | 314 | Inv. |

Based on Table 2, it is clear that the organic EL elements prepared via the metal complexes according to the present invention attain high luminescent efficiency and extended luminescent lifetime, compared to the EL element of the Comparative Examples.

Further, it was noticed that by simultaneously employing, in the emission layer, a carboline derivative or its derivative having a ring structure in which at least one carbon atom of the hydrocarbon ring constituting the carboline derivative was substituted with a nitrogen atom, targeted effects of the present invention were further enhanced.

Example 3

<Preparation of Organic EL Element 3-1>

After a substrate, in which ITO had been deposited at 150 nm on a glass plate as an anode (NA-45 produced by NH Techno Glass Co. Ltd.) was subjected to patterning, the transparent support substrate was washed with isopropyl alcohol by use of ultrasonic waves, followed by being dried with a dry nitrogen gas, and was subjected to UV ozone washing for 5 minutes.

This transparent support substrate was fixed on a substrate holder of a vacuum evaporation system available on the market, and on the other hand, each of five resistance heating boats made of tantalum was charged with m-MTDATXA, CA-2, Ir-12, BCP and Alq$_3$, respectively, which was attached in the vacuum evaporation system (in the first vacuum chamber).

Further, a resistance heating boat made of tantalum was charged with lithium fluoride and a resistance heating boat made of tungsten was charged with aluminum, respectively, and these boats were attached in the second chamber of the vacuum evaporation system.

First, after the first vacuum chamber was evacuated down to $4\times10^{-4}$ Pa, the aforesaid heating boat charged with m-MTDATXA was heated with an electric current to deposit m-MTDATXA on a support substrate at a deposition rate of 0.1-0.2 nm/sec so as to make a layer thickness of 40 nm, whereby a positive hole injection/transport layer was formed.

Further, the aforesaid heating boat charged with CA-2 and the boat charged with Ir-12 were independently supplied with an electric current to deposit CA-2 as an emission host and Ir-12 as an emission dopant so as to make a layer thickness of 30 nm while adjusting the deposition rates thereof to 100:6, whereby an emission layer was formed.

Next, the aforesaid heating boat charged with BCP was heated with an electric current to provide a positive hole inhibition layer having a layer thickness of 10 nm at a deposition rate of 0.1-0.2 nm/sec. Further, the aforesaid heating boat charged with Alq$_3$ was heated with an electric current to provide an electron transport layer having a layer thickness of 20 nm at a deposition rate of 0.1-0.2 nm/sec.

Next, after an element having been deposited with up to an electron injection layer as described before was transferred into the second vacuum chamber while keeping vacuum, a mask, which was made of stainless steel and had rectangular holes, was arranged on the electron injection layer by means of remote control from outside of the system.

After the second vacuum chamber was evacuated down to $2\times10^{-4}$ Pa, a boat charged with lithium fluoride was supplied with an electric current to provide a cathode buffer layer having a layer thickness of 0.5 nm at a deposition rate of 0.01-0.02 nm/sec, and then a boat charged with aluminum was supplied with an electric current to provide a cathode having a layer thickness of 150 nm at a deposition rate of 1-2 nm/sec to obtain Organic EL Element 3-1.

<Preparation of Organic EL Elements 3-2 to 3-18>

Organic EL elements 3-2 to 3-18 each were prepared in a similar manner to preparation of organic EL element 3-1 described above, except that an emission dopant was changed as shown in Table 3.

<<Evaluation of Organic EL Elements>>

When resulting Organic EL Elements 3-1 to 3-18 were evaluated, after their preparation, the non-luminescent side was covered with a glass case, and a 300 μm thick glass substrate was employed as a sealing substrate. Further, an epoxy based radiation curable type adhesive (LAXTRACK C0629B, produced by TOAGOSEI Co., Ltd.) was applied to the periphery as a sealing agent. The resulting substrate was overlapped onto the above anode to come into close contact with the above transparent supporting substrate. Subsequently, UV radiation was exposed to the glass substrate side to result in curing and sealing. Thus, the lighting device as shown in FIGS. 5 and 6 was formed and evaluation was then carried out.

FIG. 5 is a schematic view of a lighting device. Organic EL element 101 is covered with glass cover 102 (sealing operation employing the glass cover was carried out in a globe box (under an atmosphere of high purity nitrogen gas at a purity of at least 99.999%) without contact with atmospheric air). FIG. 6 is a sectional view of the lighting device, in which numeral 105 represents a cathode, 106 represents an organic EL layer, and 107 represents a glass substrate having a transparent electrode. Further, nitrogen gas 108 is fed into glass cover 102, and desiccant 109 is provided.

Taking-out quantum efficiency was evaluated in the same manner as for Example 1. The taking-out quantum efficiency was expressed by relative values when each value of Organic EL Element 3-1 was 100.

Table 3 shows the results.

TABLE 3

| Organic EL Element No. | Emission host | Emission dopant | *1 | Taking-out Quantum Yield | Luminescent Lifetime ($\tau_{1/2}$) | Remarks |
|---|---|---|---|---|---|---|
| 3-1 | CA-2 | Ir-12 | BCP | 100 | 100 | Comp. |
| 3-2 | CA-2 | Comparison 1 | BCP | 80 | 104 | Comp. |
| 3-3 | CA-2 | Comparison 2 | BCP | 91 | 95 | Comp. |
| 3-4 | CA-2 | Comparison 3 | BCP | 103 | 80 | Comp. |
| 3-5 | CA-2 | 3-1 | BCP | 130 | 271 | Inv. |
| 3-6 | CA-2 | 3-6 | BCP | 124 | 277 | Inv. |
| 3-7 | CA-4 | 3-10 | BCP | 126 | 256 | Inv. |
| 3-8 | CA-4 | 3-11 | BCP | 128 | 255 | Inv. |
| 3-9 | CA-2 | 3-13 | BCP | 129 | 280 | Inv. |
| 3-10 | CA-10 | 4-8 | BCP | 120 | 235 | Inv. |
| 3-12 | CA-10 | 4-9 | BCP | 122 | 245 | Inv. |
| 3-13 | CA-10 | 3-2 | CA-23 | 133 | 320 | Inv. |
| 3-14 | CA-6 | 3-8 | CA-29 | 129 | 314 | Inv. |
| 3-15 | CA-6 | 3-10 | CA-23 | 129 | 302 | Inv. |
| 3-16 | CA-6 | 3-12 | CA-29 | 122 | 262 | Inv. |
| 3-17 | CA-2 | 3-13 | CA-5 | 128 | 319 | Inv. |
| 3-18 | CA-4 | 4-9 | CA-29 | 126 | 283 | Inv. |

*1: Positive Hole Blocking Material

Based on Table 3, it is clear that the organic EL elements prepared via the metal complexes according to the present invention attain high luminescent efficiency and extended luminescent lifetime, compared to the EL element of the Comparative Examples.

Further, it was noticed that by simultaneously employing, both in the emission layer and in the hole inhibition layer, a carboline derivative or its derivative having a ring structure in which at least one carbon atom of the hydrocarbon ring constituting the carboline derivative was substituted with a nitrogen atom, targeted effects of the present invention were further enhanced.

Example 4

<Preparation of Organic EL Element 4-1>

After a substrate, in which ITO had been deposited at 150 nm on a glass plate as an anode (NA-45 produced by NH Techno Glass Co. Ltd.) was subjected to patterning, the transparent support substrate was washed with isopropyl alcohol by use of ultrasonic waves, followed by being dried with a dry nitrogen gas, and was subjected to UV ozone washing for 5 minutes. This transparent support substrate was fixed on a substrate holder of a vacuum evaporation system available on the market, and on the other hand, each of five resistance heating boats made of tantalum was charged with α-NPD, Comparison 4, CA-1, Ir-1, BCP and Alq$_3$, respectively, which was attached in the vacuum evaporation system (in the first vacuum chamber).

Further, a resistance heating boat made of tantalum was charged with lithium fluoride and a resistance heating boat made of tungsten was charged with aluminum, respectively, and these boats were attached in the second chamber of the vacuum evaporation system.

First, after the first vacuum chamber was evacuated down to 4×10$^{-4}$ Pa, the aforesaid heating boat charged with α-NPD was heated with an electric current to deposit α-NPD on a support substrate at a deposition rate of 0.1-0.2 nm/sec so as to make a layer thickness of 40 nm, whereby a positive hole injection/transport layer was formed.

Then, after the first vacuum chamber was evacuated down to 4×10$^{-4}$ Pa, the aforesaid heating boat charged with Comparison 4 was heated with an electric current to deposit Comparison 4 on a support substrate at a deposition rate of 0.1-0.2 nm/sec so as to make a layer thickness of 20 nm, whereby an electron inhibition layer was formed.

Further, the aforesaid heating boat charged with CA-1 and the boat charged with Ir-1 were independently supplied with an electric current to deposit CA-1 as an emission host and Ir-1 as an emission dopant so as to make a layer thickness of 30 nm while adjusting the deposition rates thereof to 100:7, whereby an emission layer was formed.

Next, the aforesaid heating boat charged with BCP was heated with an electric current to provide a positive hole inhibition layer having a layer thickness of 15 nm at a deposition rate of 0.1-0.2 nm/sec. Further, the aforesaid heating boat charged with Alq$_3$ was heated with an electric current to provide an electron transport layer having a layer thickness of 20 nm at a deposition rate of 0.1-0.2 nm/sec.

Next, after an element having been deposited with up to an electron injection layer as described before was transferred into the second vacuum chamber while keeping vacuum, a mask, which was made of stainless steel and had rectangular holes, was arranged on the electron injection layer by means of remote control from outside of the system.

After the second vacuum chamber was evacuated down to 2×10$^{-4}$ Pa, a boat charged with lithium fluoride was supplied with an electric current to provide a cathode buffer layer having a layer thickness of 0.5 nm at a deposition rate of 0.01-0.02 nm/sec, and then a boat charged with aluminum was supplied with an electric current to provide a cathode having a layer thickness of 150 nm at a deposition rate of 1-2 nm/sec to obtain Organic EL Element 4-1.

<Preparation of Organic EL Elements 4-2 to 4-9>

Organic EL elements 4-2 to 4-9 each were prepared in a similar manner to preparation of organic EL element 4-1 described above, except that an electron inhibition material was changed as shown in Table 4.

<<Evaluation of Organic EL Elements>>

When resulting Organic EL Elements 4-1 to 4-9 were evaluated, after their preparation, the non-luminescent side was covered with a glass case, and a 300 μm thick glass substrate was employed as a sealing substrate. Further, an epoxy based radiation curable type adhesive (LAXTRACK C0629B, produced by TOAGOSEI Co., Ltd.) was applied to the periphery as a sealing agent. The resulting substrate was overlapped onto the above anode to come into close contact with the above transparent supporting substrate. Subsequently, UV radiation was exposed to the glass substrate side to result in curing and sealing. Thus, the lighting device as shown in FIGS. 5 and 6 was formed and evaluation was then carried out.

FIG. 5 is a schematic view of a lighting device. Organic EL element 101 is covered with glass cover 102 (sealing operation employing the glass cover was carried out in a globe box (under an atmosphere of high purity nitrogen gas at a purity of at least 99.999%) without contact with atmospheric air). FIG. 6 is a sectional view of the lighting device, in which numeral 105 represents a cathode, 106 represents an organic EL layer, and 107 represents a glass substrate having a transparent electrode. Further, nitrogen gas 108 is fed into glass cover 102, and desiccant 109 is provided.

Taking-out quantum efficiency was evaluated in the same manner as for Example 1. The taking-out quantum efficiency was expressed by relative values when each value of Organic EL Element 4-1 was 100.

Table 4 shows the results.

TABLE 4

| Organic EL Element No. | Electron inhibition material | Takingout Quantum Yield | Luminescent Lifetime ($\tau_{1/2}$) | Remarks |
| --- | --- | --- | --- | --- |
| 4-1 | Comparison 4 | 100 | 100 | Comp. |
| 4-2 | 1-8 | 115 | 278 | Inv. |
| 4-3 | 1-16 | 113 | 291 | Inv. |
| 4-4 | 2-10 | 120 | 201 | Inv. |
| 4-5 | 3-13 | 122 | 245 | Inv. |
| 4-6 | 4-2 | 116 | 288 | Inv. |
| 4-7 | 4-15 | 121 | 285 | Inv. |

Based on Table 4, it is clear that the organic EL elements prepared via the metal complexes according to the present invention attain high luminescent efficiency and extended luminescent lifetime, compared to the EL element of the Comparative Examples.

Example 5

<Preparation of Organic EL Element 5-1>

A cathode (at a thickness of 200 nm) composed of an indium tin oxide (ITO at an indium/tin=95/5 mol ratio) was formed on a 25 mm×25 mm×0.5 mm glass substrate under application of a direct electric current, employing a sputtering method. The surface resistance of the resulting cathode was 10Ω/□. The above surface was coated with a dichloroethane solution in which polyvinylcarbazole (being a positive hole transporting binder polymer)/Ir-13 (being a blue fluorescent ortho metal complex)/2-(4-biphenylyl-5(4-t-butylphenyl)-1, 3,4-oxazole (being an electron transport material)=200/2/50 mole ratio were dissolved, employing a spin coater, whereby a 100 nm emission layer was prepared. On the resulting organic compound layer, a mask (being a mask resulting in a luminescent area of 5 mm×5 mm), which was subjected to patterning, was arranged and an anode was arranged in such a manner that in a vacuum evaporation device, 0.5 mm lithium fluoride was evaporated as an anode buffer layer and 150 nm aluminum as a cathode was evaporated, whereby Blue Luminescent Organic EL Element 5-1 was prepared.

<Preparation of Organic EL Elements 5-2 to 5-5>

Organic EL Elements 5-2 to 5-5 were prepared in the same manner as Organic EL Element 5-1, except that the emission dopant was changed as described in Table 5.

<<Evaluation of Organic EL Elements>>

When resulting Organic EL Elements 5-1 to 5-5 were evaluated, after their preparation, the non-luminescent side was covered with a glass case, and a 300 μm thick glass substrate was employed as a sealing substrate. Further, an epoxy based radiation curable type adhesive (LAXTRACK C0629B, produced by TOAGOSEI Co., Ltd.) was applied to the periphery as a sealing agent. The resulting substrate was overlapped onto the above anode to come into close contact with the above transparent supporting substrate. Subsequently, UV radiation was exposed to the glass substrate side to result in curing and sealing. Thus, the lighting device as shown in FIGS. 5 and 6 was formed and evaluation was then carried out.

FIG. 5 is a schematic view of a lighting device. Organic EL element 101 is covered with glass cover 102 (sealing operation employing the glass cover was carried out in a globe box (under an atmosphere of high purity nitrogen gas at a purity of at least 99.999%) without contact with atmospheric air). FIG. 6 is a sectional view of the lighting device, in which numeral 105 represents a cathode, 106 represents an organic EL layer, and 107 represents a glass substrate having a transparent electrode. Further, nitrogen gas 108 is fed into glass cover 102, and desiccant 109 is provided.

Subsequently, luminance and luminescent efficiency were determined as described below.
(Luminance and Luminescent Efficiency)

By employing SOURCE MAJOR UNIT Type 2400, produced by Toyo Technica Inc., DC voltage was applied to an organic EL element to result in luminescence. Luminance ($cd/m^2$) in the case in which 10 V DC voltage was applied, was determined and luminescent efficiency (lm/W). In the case in which an electric current of 2.5 $mA/cm^2$ was run, was also determined.

Table 5 shows the results.

TABLE 5

| Organic EL Element No. | Emission dopant | Luminance ($cd/m^2$) | Luminescent Efficiency (lm/W) | Remarks |
|---|---|---|---|---|
| 5-1 | Ir-13 | 100 | 100 | Comparative Example |
| 5-2 | 1-2 | 118 | 185 | Present Invention |
| 5-3 | 2-8 | 113 | 190 | Present Invention |
| 5-4 | 3-11 | 114 | 189 | Present Invention |
| 5-5 | 4-2 | 115 | 173 | Present Invention |

Based on Table 5, it is evident that the organic EL elements prepared by employing the metal complexes according to the present invention attained high luminescent efficiency and high luminance, compared to the EL element of the Comparative Example.

Example 6

<Preparation of Full-Color Display Device>
(Preparation of Blue Emission Element)

Organic EL element 1-5 of example 1 was utilized as a blue emission element.
(Preparation of Green Emission Element)

Organic EL element 4-7 of example 4 was utilized as a green emission element.

(Preparation of Red Emission Element)

A red emission element was prepared by substituting Ir-13 used in Organic EL element 2-1 of Example 2 with Ir-9.

Each of red, green and blue organic EL elements prepared above was arranged parallel on the same substrate to prepare an active matrix mode full-color having a form as described in FIG. 1, and only display section A of said display device is schematically shown in FIG. 2. That is, a wiring section containing plural lines of scanning line 5 and data line 6, and plural pixels 3 (such as a pixel having an emission color of a red region, a pixel of a green region and a pixel of a blue region) arranged parallel are provided on the same substrate, and scanning lines 5 and data lines 6 in a wiring section, which are comprised of a conductive material, respectively, cross each other at a right angle in a grid form to be connected to pixels 3 at the right-angled crossing points (details being not shown in the drawing). The aforesaid plural pixels 3 each are operated in an active matrix mode, in which an organic EL element, a switching transistor and an operating transistor are provided corresponding to each emission color, and receive an image data signal from data line 6 when a scanning signal is applied from scanning line 5 to emit based on the received image data. Each red, green and blue pixel was appropriately arranged parallel in this manner, whereby a full-color display device was prepared.

It has been proved that a full-color moving image display device exhibiting a high luminance, a high durability and a highly visibility can be achieved by operating said full-color display.

Example 7

<Preparation of White Emitting Element and White Lighting>Device

A transparent electrode substrate of example 1 was subjected to patterning of an electrode having an area of 20 mm×20 mm, and α-NPD was deposited thereon at a layer thickness of 25 nm as a positive hole injection/transport layer in a similar manner to example 1; and further the aforesaid heating boat charged with CA-1, boat containing Example compound (1-11) and boat containing Ir-9 were supplied with an electric current to deposit an emission layer having a layer thickness of 30 nm, while adjusting the evaporation rates of CA-1 as an emission host, Example compound (1-11) and Ir-9 as emission dopants to be 100:5:0.6.

Successively, BCP was deposited at 10 nm to provide a positive hole inhibition layer. Further, $Alq_3$ was deposited at 40 nm to provide an electron transport layer.

Next, similar to example 1, a mask with square holes having a shape nearly same as a transparent electrode made of stainless steel was arranged on an electron injection layer, and 0.5 nm of lithium fluoride as a cathode buffer layer and 150 nm of aluminum as a cathode were deposited.

This element was equipped with a sealed can, which had a similar structure and was prepared in a similar method to example 1, to prepare flat lamps shown in FIGS. 5 and 6. FIG. 5 shows a schematic view of a lighting device, and FIG. 6 shows a cross-sectional view of a lighting device.

FIG. 5 is a schematic view of a lighting device. Organic EL element 101 is covered with glass cover 102 (sealing operation employing the glass cover was carried out in a globe box (under an atmosphere of high purity nitrogen gas at a purity of at least 99.999%) without contact with atmospheric air). FIG. 6 is a sectional view of the lighting device, in which numeral 105 represents a cathode, 106 represents an organic EL layer, and 107 represents a glass substrate having a transparent electrode. Further, nitrogen gas 108 is fed into glass cover 102, and desiccant 109 is provided.

Nearly white light was obtained when these lamps were supplied with an electric current to prove that said lamp can be utilized as a lighting device.

What is claimed is:

1. An organic electroluminescent element material comprising a metal complex having a partial structure represented by Formula (1):

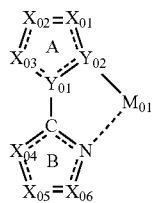

Formula (1)

wherein $X_{01}$, $X_{02}$, $X_{03}$, and $X_{06}$ each represent $CR_{01}$, a nitrogen atom, $NR_{02}$, an oxygen atom or a sulfur atom, $X_{04}$ represents $CR_{01}$ and $X_{05}$ represents a nitrogen atom; $Y_{01}$ and $Y_{02}$ each represent a carbon atom or a nitrogen atom; $R_{01}$ and $R_{02}$ each represent a hydrogen atom, an alkyl group, an aromatic hydrocarbon ring group or an aromatic heterocyclic ring group, provided that at least one of $X_{01}$, $X_{02}$, $X_{03}$, and $X_{06}$ represents $CR_{01}$ in which $R_{01}$ is an aromatic hydrocarbon ring group or an aromatic heterocyclic ring group; $M_{01}$ represents an Ir atom or a Pt atom; rings A and B each represent a single five-membered ring, and bonds to form each of rings A and B represent a single bond or a double bond.

2. The organic electroluminescent element material of claim 1,
wherein $X_{01}$ represents a sulfur atom.

3. The organic electroluminescent element material of claim 1,
wherein $X_{01}$ represents an oxygen atom.

4. The organic electroluminescent element material of claim 1,
wherein $X_{02}$ represents a nitrogen atom.

5. The organic electroluminescent element material of claim 1,
wherein $X_{02}$ represents a sulfur atom.

6. The organic electroluminescent element material of claim 1,
wherein $X_{02}$ represents an oxygen atom.

* * * * *